US010052369B2

(12) United States Patent
Scoles et al.

(10) Patent No.: US 10,052,369 B2
(45) Date of Patent: Aug. 21, 2018

(54) AQUAPORIN 2 PROTECTS CATTLE FROM TICKS AND TICK-BORNE PARASITES

(71) Applicants: The United States of America as represented by the Secretary of Agriculture, Washington, DC (US); Washington State University

(72) Inventors: Glen A. Scoles, Moscow, ID (US); Felicito Guerrero, Boerne, TX (US); Reginaldo Bastos, Pullman, WA (US)

(73) Assignees: The United States of America, as represented by the Secretary of Agriculture, Washington, DC (US); Washington State University, Pullman, WA (US)

( * ) Notice: Subject to any disclaimer, the term of this patent is extended or adjusted under 35 U.S.C. 154(b) by 0 days.

(21) Appl. No.: 15/177,865

(22) Filed: Jun. 9, 2016

(65) Prior Publication Data

US 2016/0361396 A1    Dec. 15, 2016

Related U.S. Application Data

(60) Provisional application No. 62/172,985, filed on Jun. 9, 2015.

(51) Int. Cl.
*A61K 39/00* (2006.01)
*C07K 14/435* (2006.01)

(52) U.S. Cl.
CPC .... *A61K 39/0003* (2013.01); *C07K 14/43527* (2013.01); *A61K 2039/552* (2013.01); *A61K 2039/55566* (2013.01)

(58) Field of Classification Search
None
See application file for complete search history.

(56) References Cited

U.S. PATENT DOCUMENTS

| 8,722,063 B2 | 5/2014 | Guerrero, Jr. et al. |
| 9,408,896 B2 | 8/2016 | Guerrero et al. |
| 2008/0317786 A1 | 12/2008 | Suarez et al. |

OTHER PUBLICATIONS

Ball et al., "Identification, functional characterization and expression patterns of a water-specific aquaporin in the brown dog tick, *Rhipicephalus sanguineus*," Insect Biochemistry and Molecular Biology, (2009), 39: 105-112.

(Continued)

*Primary Examiner* — Robert A Zeman
(74) *Attorney, Agent, or Firm* — David L. Marks; John D. Fado; Gail E. Poulos

(57) ABSTRACT

A novel method of using an aquaporin protein from *Rhipicephalus microplus* (RmAQP2), fragments of RmAQP2, and/or the cDNA encoding RmAQP2 and/or the fragments are described. Immunogenic composition containing recombinant RmAQP2 and/or fragments of RmAQP2 are produced and administered to an ungulate which generates an immune response to RmAQP2. After feeding female ticks on the ungulate injected with RmAQP2 and/or fragments of RmAQP2, the female ticks have lower reproductive viability because of a reduced egg mass, reduced hatching percentage, and reduced survival of larvae. Thus, administering RmAQP2 and/or RmAQP2 fragments to an ungulate can reduce the incidence of *R. microplus* and also reduce the incidence of tick-borne pathogens in ungulates because of the lower number of *R. microplus*.

9 Claims, 3 Drawing Sheets

(56) References Cited

OTHER PUBLICATIONS

Guerrero et al., "Rhipicephalus (Boophilus) microplus aquaporin as an effective vaccine antigen to protect against cattle tick infestations," Parasites & Vectors, (2014), 7:475 pp. 1-12
Hussein et al., "Targeted silencing of the Aquaporin 2 gene of Rhipicephalus (Boophilus) microplus reduces tick fitness," Parasites & Vectors, (2015), 8:618 pp. 1-12.
Rachinshky et al., "Proteomic profiling of Rhipicephalus (Boophilus) microplus midgut responses to infection with Babesia bovis," ScienceDirect: Veterinary Parasitology, (2008), 152:294-313.
Seixas et al., "Rhipicephalus (Boophilus) microplus embryo proteins as target for tick vaccine," Veterinary Immunology and Immunopathology, (2012), 148: 149-156.
Contreras, Marinela et al., Control of infestations by *Ixodes ricinus* tick larvae in rabbits vaccinated , Vaccine, (2017), 35: 1323-1328.

AQUAPORIN 2 PROTECTS CATTLE FROM TICKS AND TICK-BORNE PARASITES

CROSS-REFERENCE TO RELATED APPLICATIONS

This application claims the benefit under 35 U.S.C. § 119(e) to U.S. Patent Application 62/172,985 filed on Jun. 9, 2015, the contents of which are incorporated herein by reference in its entirety.

BACKGROUND OF THE INVENTION

Field of the Invention

This invention relates to a novel protein/antigen, aquaporin 2, from *Rhipicephalus microplus* and immunogenic compositions containing this protein/antigen. This invention also relates to methods for protecting cattle from bovine babesiosis, a disease caused by *Babesia bovis*, which is transmitted to cattle during feeding of *R. microplus*, the vector of *B. bovis*.

Description of Related Art

Aquaporin (AQP) is a transmembrane protein family that forms pores to transport water and small solutes across cellular membranes (Borgnia, et al., *Annu. Rev. Biochem.* 68:425-458 (1999)). Members of the AQP family have been identified throughout the plant and animal kingdoms (Gonen and Walz, *Quarterly Reviews of Biophysics* 39:361-396 (2006)). AQP structures are conserved among species, having six transmembrane domains that are connected by two intracellular loops and three extracellular loops. Two asparagine-proline-alanine (NPA) motifs are considered AQP signature motifs and are located at the protein portion that interacts to form a pore (Borgnia, et al. (1999)). A total of 13 AQP members have been identified so far and classed into two subsets: those permeated by water and those permeated by water plus other small molecules, such as glycerol and urea (Borgnia, et al. (1999); Gonen and Walz (2006)).

Numerous members of the AQP family have been identified in arthropods in the last few years because of the availability of several arthropod genomes and genetic information, such as transcriptomes and cDNA libraries (Benoit, et al., *J. Comp. Physiol. B.* 184(7):811-25 (2014)). Studies have shown that AQPs play a pivotal role in arthropods, especially in blood-feeding species, such as mosquitoes and ticks. In fact, blood-feeding arthropods have become a model for AQP research because of the critical relevance that osmoregulation plays during feeding (Campbell, et al., *J. Comp. Physiol. B.* 178:935-955 (2008)). Tick females ingest up to 100 times their body weight in blood, returning approximately 75% of the ingested water and ions via their saliva into the host (Kaufman and Philips, *J. Exp. Biol.* 58:523-536 (1973)). Therefore, the osmoregulatory system of ticks is central for their life cycle and has implications for efficient feeding and subsequent generation of viable offspring.

The cattle tick *Rhipicephalus* (*Boophilus*) *microplus* is one of the most economically important ectoparasites of bovines, as it is the main vector implicated in the transmission of the apicomplexan protozoan *Babesia bovis*, the etiological agent of bovine babesiosis (Friedhoff, K T, *Transmission of babesia*, pp. 23-52 in *Babesiosis of Domestic Animals and Man*, ed.: Ristic, CRC Press (Boca Raton, Fla.) (1988)). *R. microplus* adult females acquire *B. bovis* merozoites by ingesting blood from an infected bovine and pass the protozoan transovarially to their larval progeny which then transmit *B. bovis* sporozoites to naïve cattle during subsequent feeding (Friedhoff (1988); Mahoney and Mine, *Res. Vet. Sci.* 26:253-254 (1979); Bock, et al., *Parasitology* 129(Suppl):5247-5269 (2004)). Currently, control of bovine babesiosis relies mainly on targeting tick populations and on the use of live attenuated vaccines in most endemic areas (Friedhoff (1988); Mahoney, et al. (1979); Bock, et al. (2004)). The control of *R. microplus* is mainly based on the use of acaricides and, to a much lesser extent, by anti-tick vaccination (Fragoso, et al., *Vaccine* 16:1990-1992 (1998); Jonsson, et al., *Vet. Parasitology* 88:275-285 (2000)). However, the efficacy of commercial anti-tick vaccines is inconsistent in different regions of the world. Furthermore, the recent development of tick populations resistant to acaricides represents a serious threat to the cattle industry (Miller, et al., *J. Med. Entomol.* 42:912-917 (2005); de la Fuente, et al., *Animal Health Research Reviews* 8:23-28 (2007)). Additionally, the reemergence of *R. microplus* in areas that had been considered to be free of this tick, such as the regions outside the permanent quarantine zone in south Texas, is causing concerns about the reintroduction of *B. bovis* into areas currently free of bovine babesiosis. Exposure of naïve cattle in these areas to *B. bovis* would lead to significant mortality since no herd immunity is present in the population.

U.S. Pat. No. 8,722,063 covers *R. microplus* aquaporin 1 (RmAQP1) and the use of RmAQP1 as an antigen to reduce tick viability and reproduction.

A second aquaporin protein from *R. microplus* (RmAQP2) was recently identified. See, Guerrero, et al., *Insect Biochemistry and Molecular Biology* 35:585-595 (2005); and Guerrero, et al., *Parasites & Vectors* 7:475 (2014). RmAQP2 is 42% identical to RmAQP1 at the amino acid level but 85% identical at the amino acid level to a *Dermacentor variabilis* aquaporin. See, Guerrero, et al. (2014). RmAQP1 is expressed in tick synganglia. In contrast, RmAQP2 is expressed in salivary glands.

As such a vaccine that is effective against *R. microplus* that would also prevent transmission of tick-borne pathogen, *B. bovis*, is vital. Because intake of blood meals leading to full engorgement of adult females and generation of viable larval offspring are critical steps of the tick life cycle, perhaps attempts to disrupt the feeding process can result in a vaccine with better efficacy than the currently marketed vaccines.

BRIEF DESCRIPTION OF THE INVENTION

It is an object of this invention to have an aquaporin 2 protein from *Rhipicephalus microplus* referred to as RmAQP2, fragment thereof, and polynucleotides encoding the aquaporin 2 protein and/or fragments thereof. RmAQP2, fragments thereof, and polynucleotides (including expression vectors) encoding RmAQP2 and/or fragments thereof are also referred to a *R. microplus* immunogen, depending on the context of the sentence. It is another object of this invention to have an immunogenic composition containing a *R. microplus* immunogen, a pharmaceutically acceptable carrier, and optionally an adjuvant which can be administered to ungulates and which reduces the viability of the tick's offspring, thereby reducing infestation of ungulate by the ticks, and also thereby reducing prevalence in ungulates of diseases for which *R. microplus* is a vector/host and reducing disease transmission by *R. microplus*. One such disease is caused by *Babesia bovis*, a parasite. Other diseases can be caused by bacteria, viruses, or other parasites.

It is a further object of this invention to have a method for reducing the viability of the offspring of *R. microplus* by administering to an ungulate an immunogenic composition containing a R. microplus immunogen, a pharmaceutically acceptable carrier, and optionally an adjuvant, in an amount sufficient to induce an immune response in the ungulate to RmAQP2 (and/or fragment thereof) such that the immune response causes a decrease in the viability of the offspring of R. microplus that feed on the immunized ungulate, as compared to the viability of the offspring of R. microplus that feed on a non-immunized ungulate. It is a further object of this invention that the R. microplus immunogen is RmAQP2 which has an amino acid sequence of SEQ ID NO: 2, amino acids 3-293 of SEQ ID NO: 2, SEQ ID NO: 5, SEQ ID NO: 7, SEQ ID NO: 9, and/or an amino acid sequence that is at least 95% identical to SEQ ID NO: 2, amino acids 3-293 of SEQ ID NO: 2, SEQ ID NO: 5, SEQ ID NO: 7, and/or SEQ ID NO: 9. It is another object of this invention that the R. microplus immunogen is a fragment of RmAQP2 and has the amino acid sequence of SEQ ID NO: 13, SEQ ID NO: 14, SEQ ID NO: 15, and/or SEQ ID NO: 27. It is another object of this invention that the R. microplus immunogen is a polynucleotide encoding RmAQP2 or fragments of RmAQP2 (and expression vectors containing the polynucleotide) such that it encodes the amino acids sequences described herein. Alternatively, the R. microplus immunogen is a polynucleotide encoding RmAQP2 (and expression vectors containing the polynucleotide) and having the DNA sequence of SEQ ID NO: 1, SEQ ID NO: 3, nucleotides 7-882 of SEQ ID NO: 3, SEQ ID NO: 4, nucleotides 7-879 of SEQ ID NO: 4, nucleotides 7-882 of SEQ ID NO: 4, SEQ ID NO: 6, SEQ ID NO: 8, and/or SEQ ID NO: 10; and a polynucleotide encoding a fragment of RmAQP2 (and expression vectors containing the polynucleotide) having the sequence of SEQ ID NO: 24, SEQ ID NO: 25, SEQ ID NO: 26, and/or SEQ ID NO: 28. It is another object of the invention that the ungulate that is immunized or is injected with the immunogenic composition is a ruminant.

It is further object of this invention to have method for reducing the incidence of R. microplus infestation of an ungulate by administering to the ungulate an immunogenic composition containing a R. microplus immunogen, a pharmaceutically acceptable carrier, and optionally an adjuvant, in an amount sufficient to generate an immune response in the ungulate to RmAQP2 or a fragment thereof, such that the immune response reduces the number of viable offspring of R. microplus that feed on the ungulate immunized with (or injected with) the immunogenic composition, as compared to the viability of the offspring of R. microplus that feed on a non-immunized ungulate. The R. microplus immunogen can be RmAQP2, at least one fragment of RmAQP2, DNA encoding RmAQP2, DNA encoding a fragment of RmAQP2, and expression vectors containing the DNA. Thus, this method also reduces the number of R. microplus in an area over time which will reduce tick infestation rates. This method also reduces the transmission of diseases for which R. microplus is a host/vector. It is a further object of this invention that RmAQP2 has an amino acid sequence of SEQ ID NO: 2, amino acids 3-293 of SEQ ID NO: 2, SEQ ID NO: 5, SEQ ID NO: 7, and/or SEQ ID NO: 9, or an amino acid sequence that is at least 95% identical to SEQ ID NO: 2, amino acids 3-293 of SEQ ID NO: 2, SEQ ID NO: 5, SEQ ID NO: 7, and/or SEQ ID NO: 9. It is another object of this invention that the fragment of RmAQP2 has the amino acid sequence of SEQ ID NO: 13, SEQ ID NO: 14, SEQ ID NO: 15, and/or SEQ ID NO: 27. It is another object of this invention that the polynucleotide encoding RmAQP2 or fragments of RmAQP2 is such that it encodes the amino acids sequences described herein. Alternatively, the polynucleotide encoding RmAQP2 has the sequence of SEQ ID NO: 1, SEQ ID NO: 3, nucleotides 7-882 of SEQ ID NO: 3, SEQ ID NO: 4, nucleotides 7-882 of SEQ ID NO: 4, SEQ ID NO: 6, SEQ ID NO: 8, and/or SEQ ID NO: 10; and the polynucleotide encoding the fragment of RmAQP2 has the sequence of SEQ ID NO: 24, SEQ ID NO: 25, SEQ ID NO: 26, and/or SEQ ID NO: 28. It is another object of the invention that the ungulate that is immunized or is injected with the immunogenic composition is a ruminant.

It is a further object of this invention to have an expression vector that contains the polynucleotide that encodes RmAQP2 or RmAQP2 fragments operably linked to a heterologous promoter. It is another object of the invention to have a recombinant organism that contains the expression vector that contains the polynucleotide that encodes RmAQP2 or RmAQP2 fragments operably linked to a heterologous promoter. This recombinant organism can be a bacterium or yeast or *Babesia* spp. It is a further object of this invention that the immunogenic compositions and methods of using the immunogenic compositions describe herein contain the expression vector(s) which contain a heterologous promoter operably linked to a polynucleotide encoding RmAQP2 or fragments thereof which are described herein.

It is another object of this invention to have a kit with a first container which holds a R. microplus immunogen, instructions for administering the R. microplus immunogen to an ungulate, and optionally a second container holding an adjuvant, and optionally a third container holding a pharmaceutically acceptable carrier. The R. microplus immunogen can be one of the RmAPQ2 described herein, a fragment of RmAQP2 described herein, polynucleotides (and/or expression vectors) encoding RmAQP2 and/or a fragment of RmAQP2 described herein, or a combination thereof.

BRIEF DESCRIPTION OF THE FIGURES

FIG. 3A shows the level of gene silencing of ticks injected with one RmAQP2 dsRNA fragment (397 bp, SEQ ID NO: 19). FIG. 3B shows the level of gene silencing of ticks injected with two RmAQP2 dsRNA fragments (397 bp, SEQ ID NO: 19 and 396 bp, SEQ ID NO: 23).

DETAILED DESCRIPTION OF THE INVENTION

Figure 1:
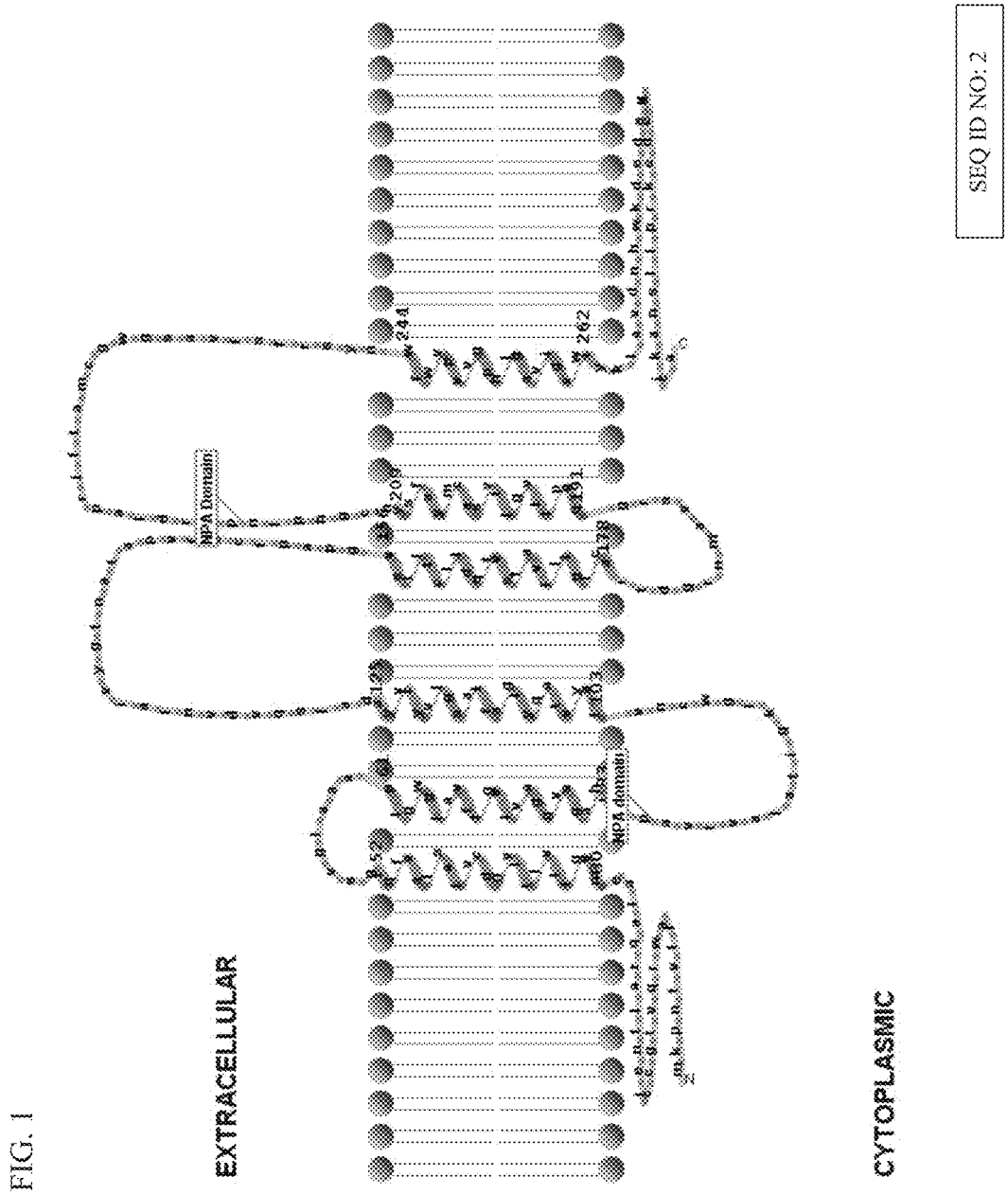
FIG. 1 shows the topology prediction of RmAQP2 (SEQ ID NO: 2) indicating the presence of 6 transmembrane-spanning regions, 3 extracellular loops, 2 intracellular loops and two NPA AQP signature domains.

The present invention involves a newly identified aquaporin gene (and the protein encoded by the DNA) present in R. microplus referred to as RmAQP2. This gene is transcribed in unfed larvae, engorged nymphs, and salivary glands and guts of partially engorged females. RmAQP2 protein is present in salivary glands of partially engorged females. An immunogenic composition containing RmAQP2, alone or in combination of other aquaporin proteins or other disease antigens, and optionally adjuvant and pharmaceutically acceptable carrier, after administration to an ungulate, will generate an immune response in the ungulate. After ticks feed on the immunized ungulate, the ticks' reproduction rate is reduced (a lower number of eggs are laid, a lower number of eggs hatch, and/or lower number of larvae survive, compared to ticks that feed on non-immunized ungulates). This reduction in tick reproduction results in fewer ticks and thus fewer carriers for tick-borne pathogens, such as *B. bovis*. In turn, fewer cattle become infected with *B. bovis* and other tick-borne pathogens. Table 1, infra, lists the various forms of RmAQP2 and polynucleotides involved with this invention. It is noted that the amino acid sequence of RmAQP2 produced in *Pichia pastoris* (SEQ ID NO: 7) differs from the amino acid sequence (SEQ ID NO: 2) of the longest open reading frame of RmAQP2 cDNA obtained from *R. microplus*. In particular, the second amino acid in SEQ ID NO: 7 is different from the second amino acid of SEQ ID NO: 2, and SEQ ID NO: 7 has two additional amino acids at the carboxyl terminus. As such, amino acids 3-293 in both SEQ ID NO: 2 and SEQ ID NO: 7 are identical. Further, nucleotides 7-882 of SEQ ID NO: 3 and nucleotides 7-882 of SEQ ID NO: 4 encode amino acids 3-293 of SEQ ID NO: 2 and SEQ ID NO: 7.

Thus, in one embodiment, this invention involves an immunogenic composition containing a *R. microplus* immunogen, a pharmaceutically acceptable carrier, and optionally an adjuvant. In one embodiment, the *R. microplus* immunogen is RmAQP2 and/or at least one fragment of RmAQP2. In another embodiment, the *R. microplus* immunogen is an expression vector containing a heterologous promoter operably linked to a polynucleotide encoding RmAQP2 and/or at least one fragment of RmAQP2. In another embodiment, this invention involves an immunogenic composition containing a *R. microplus* immunogen and one or more other tick proteins, a pharmaceutically acceptable carrier, and optionally an adjuvant. One such possible other tick protein is RmAQP1. In another embodiment, the *R. microplus* immunogen is a dsRNA having a sequence of SEQ ID NO: 19 and/or SEQ ID NO: 22. In another embodiment, the *R. microplus* immunogen is an expression vector that produces dsRNA which has a sequence of RmAQP2 or a fragment thereof with SEQ ID NO: 19 and SEQ ID NO: 22 being just two possible sequences of the dsRNA.

Another embodiment of this invention involves genetically altered *Babesia* spp. that contain heterologous DNA which encode RmAQP2 or at least one fragment of

TABLE 1 cDNA sequence of RmAQP2 from *R. microplus* (SEQ ID NO: 1)
Amino acid sequence of longest open reading frame of prior RmAQP2 cDNA (SEQ ID NO: 2)
DNA sequence of non-optimized RmAQP2 for cloning into pPIC (SEQ ID NO: 3)
DNA sequence of codon optimized RmAQP2 for cloning into pPIC and expression in *Pichia pastoris* (SEQ ID NO: 4)
Amino acid sequence of codon optimized RmAQP2 (SEQ ID NO: 5)
DNA sequence of EcoRI-RmAQP2-NotI codon optimized for expression in *P. pastoris* (SEQ ID NO: 6)
Amino acid sequence of open reading frame of codon optimized EcoRI-RmAQP2-NotI (SEQ ID NO: 7)
Open reading frame of EcoRI-RmAQP2-NotI codon optimized in pPIC expression vector (SEQ ID NO: 8)
Amino acid sequence of open reading of EcoRI-RmAQP2-NotI codon optimized in pPIC expression vector (includes HIS tag) (SEQ ID NO: 9)
Degenerate RmAQP2 DNA sequence (SEQ ID NO: 10)
Amino acid sequence of Peptide 1 (10-mer) (SEQ ID NO: 13)
DNA sequence of Peptide 1 (SEQ ID NO: 24)
Amino acid sequence of Peptide 2 (32-mer) (SEQ ID NO: 14)
DNA sequence of Peptide 2 (SEQ ID NO: 25)
Amino acid sequence of Peptide 3 (19-mer) (SEQ ID NO: 15)
DNA sequence of Peptide 3 (SEQ ID NO: 26)
Amino acid sequence of Peptide 4 (14-mer) SEQ ID NO: 27
DNA sequence of Peptide 4 SEQ ID NO: 28

As described below, in-vivo assays demonstrate that RmAQP2 silencing significantly reduces tick fitness, and this effect is even more dramatic in females fed on a calf during acute *B. bovis* infection. Further, injecting cattle with RmAQP2 also reduces tick fitness and reproduction rates. As such, immunogenic compositions containing RmAQP2 and/or RmAQP2 fragments and immunogenic compositions containing DNA that encode RmAQP2 and/or RmAQP2 fragments can be useful in reducing the rate of *B. bovis* disease transmission and other tick-borne pathogens.

In addition to *B. bovis*, *R. microplus* also transmits *B. bigemina* transovarially, and it transmits *Anaplasma marginale* both transstadially and intrastadially. So, for the *Babesia*, reducing reproductive output reduces the number of larvae that might be available to transmit these parasites. For all three pathogens reducing reproductive output will reduce the overall tick burden, which should also indirectly reduce the transmission rate (i.e., fewer ticks equals less pathogen transmission).

RmAQP2 operably linked to a promoter. These genetically altered *Babesia* spp. produce RmAQP2 or the fragment(s) of RmAQP2. One embodiment of this invention is described in U.S. Patent App. Publication US 2008/0317786. In one embodiment, the genetically altered *Babesia* spp. contains an expression vector which contains a polynucleotide of SEQ ID NO: 18 and/or SEQ ID NO: 22 which is operably linked to a promoter on the positive strand of the expression vector and to a second promoter on the negative strand of the expression vector such that a dsRNA can be produced. Such dsRNA then has the sequence of SEQ ID NO: 19 and/or SEQ ID NO: 23, respectively. Alternatively, the genetically altered *Babesia* spp. contains an expression vector having polynucleotide of SEQ ID NO: 18 and the reverse complement thereof; and/or SEQ ID NO: 22 and the reverse complement thereof; linked to one or two promoters such that dsRNA having sequence of SEQ ID NO: 19 and/or SEQ ID NO: 23, respectively, can be produced. Any of these genetically altered *Babesia* spp. can be administered to an animal so that the genetically altered *Babesia* spp. produce the desired polynucleotide and/or peptide which reduces with tick's reproduction and/or survival.

In yet another embodiment of this invention, the use of one or more of these immunogenic compositions reduces the transmission of various parasites (such as, but not limited to, *B. bovis, B. bigemina*, and *A. marginale*) to cattle and other ungulates. In a further embodiment of this invention, the use of one or more of these immunogenic compositions reduces the number of viable *R. microplus* offspring and/or reduces the number of *R. microplus* in an area.

In another embodiment, this invention involves a kit containing a first container, optionally a second container, and instructions on mixing and/or administering the immunogenic composition. RmAQP2, at least one fragment of RmAQP2, DNA encoding RmAQP2 and/or DNA encoding at least one fragment of RmAQP2 (the *R. microplus* immunogen) are present in the first container. The optional second container has a pharmaceutically acceptable carrier. Another optional container holds an adjuvant. Optional additional container(s) can hold RmAQP1 and/or other tick protein(s) for use in the immunogenic composition.

The immunogenic composition described herein may be administered to domestic ungulates which include horses, donkeys, camels, llamas, oxen, pigs, and ruminants. Ruminants includes cattle (bovine), buffalo, sheep, goats, and deer.

Because this invention involves recombinant DNA techniques, the following definitions are provided to assist in describing this invention. The terms "isolated", "purified", or "biologically pure" as used herein, refer to material that is substantially or essentially free from components that normally accompany the material in its native state or when the material is produced. In an exemplary embodiment, purity and homogeneity are determined using analytical chemistry techniques such as polyacrylamide gel electrophoresis or high performance liquid chromatography. A nucleic acid or particular bacteria that are the predominant species present in a preparation is substantially purified. In an exemplary embodiment, the term "purified" denotes that a nucleic acid or protein that gives rise to essentially one band in an electrophoretic gel. Typically, isolated nucleic acids or proteins have a level of purity expressed as a range. The lower end of the range of purity for the component is about 60%, about 70% or about 80% and the upper end of the range of purity is about 70%, about 80%, about 90% or more than about 90%.

The term "nucleic acid" as used herein, refers to a polymer of ribonucleotides or deoxyribonucleotides. Typically, "nucleic acid" polymers occur in either single- or double-stranded form, but are also known to form structures comprising three or more strands. The term "nucleic acid" includes naturally occurring nucleic acid polymers as well as nucleic acids comprising known nucleotide analogs or modified backbone residues or linkages, which are synthetic, naturally occurring, and non-naturally occurring, which have similar binding properties as the reference nucleic acid, and which are metabolized in a manner similar to the reference nucleotides. Exemplary analogs include, without limitation, phosphorothioates, phosphoramidates, methyl phosphonates, chiral-methyl phosphonates, 2-O-methyl ribonucleotides, and peptide-nucleic acids (PNAs). "DNA", "RNA", "polynucleotides", "polynucleotide sequence", "oligonucleotide", "nucleotide", "nucleic acid", "nucleic acid molecule", "nucleic acid sequence", "nucleic acid fragment", and "isolated nucleic acid fragment" are used interchangeably herein.

For nucleic acids, sizes are given in either kilobases (kb) or base pairs (bp). Estimates are typically derived from agarose or polyacrylamide gel electrophoresis, from sequenced nucleic acids, or from published DNA sequences. For proteins, sizes are given in kilodaltons (kDa or KDa) or amino acid residue numbers. Proteins sizes are estimated from gel electrophoresis, from sequenced proteins, from derived amino acid sequences, or from published protein sequences.

Unless otherwise indicated, a particular nucleic acid sequence also implicitly encompasses conservatively modified variants thereof (e.g., degenerate codon substitutions), the complementary (or complement) sequence, and the reverse complement sequence, as well as the sequence explicitly indicated. Specifically, degenerate codon substitutions may be achieved by generating sequences in which the third position of one or more selected (or all) codons is substituted with mixed-base and/or deoxyinosine residues (see e.g., Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98(1994)). Because of the degeneracy of nucleic acid codons, one can use various different polynucleotides to encode identical polypeptides. Table 2, infra, contains information about which nucleic acid codons encode which amino acids.

TABLE 2

| Amino acid | Nucleic acid codons | Amino acid | Nucleic acid codons |
|---|---|---|---|
| Ala/A | GCT, GCC, GCA, GCG | Leu/L | TTA, TTG, CTT, CTC, CTA, CTG |
| Arg/R | CGT, CGC, CGA, CGG, AGA, AGG | Lys/K | AAA, AAG |
| Asn/N | AAT, AAC | Met/M | ATG |
| Asp/D | GAT, GAC | Phe/F | TTT, TTC |
| Cys/C | TGT, TGC | Pro/P | CCT, CCC, CCA, CCG |
| Gln/Q | CAA, CAG | Ser/S | TCT, TCC, TCA, TCG, AGT, AGC |
| Glu/E | GAA, GAG | Thr/T | ACT, ACC, ACA, ACG |
| Gly/G | GGT, GGC, GGA, GGG | Trp/W | TGG |
| His/H | CAT, CAC | Tyr/Y | TAT, TAC |
| Ile/I | ATT, ATC, ATA | Val/V | GTT, GTC, GTA, GTG |

In addition to the degenerate nature of the nucleotide codons which encode amino acids, alterations in a polynucleotide that result in the production of a chemically equivalent amino acid at a given site, but do not affect the functional properties of the encoded polypeptide, are well known in the art. "Conservative amino acid substitutions" are those substitutions that are predicted to interfere least with the properties of the reference polypeptide. In other words, conservative amino acid substitutions substantially conserve the structure and the function of the reference protein. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine or histidine, can also be expected to produce a functionally equivalent protein or polypeptide. Table 3 provides a list of exemplary conservative amino acid substitutions. Conservative amino acid substitutions generally maintain (a) the structure of the polypeptide backbone in the area of the substitution, for example, as a beta sheet or alpha helical conformation, (b) the charge or hydrophobicity of the molecule at the site of the substitution, and/or (c) the bulk of the side chain.

TABLE 3

| Amino Acid | Conservative Substitute |
|---|---|
| Ala | Gly, Ser |
| Arg | His, Lys |
| Asn | Asp, Gln, His |
| Asp | Asn, Glu |
| Cys | Ala, Ser |
| Gln | Asn, Glu, His |
| Glu | Asp, Gln, His |
| Gly | Ala |
| His | Asn, Arg, Gln, Glu |
| Ile | Leu, Val |
| Leu | Ile, Val |
| Lys | Arg, Gln, Glu |
| Met | Ile, Leu |
| Phe | His, Leu, Met, Trp, Tyr |
| Ser | Cys, Thr |
| Thr | Ser, Val |
| Trp | Phe, Tyr |
| Tyr | His, Phe, Trp |
| Val | Ile, Leu, Thr |

Oligonucleotides and polynucleotides that are not commercially available can be chemically synthesized e.g., according to the solid phase phosphoramidite triester method first described by Beaucage and Caruthers, *Tetrahedron Letts.* 22:1859-1862 (1981), or using an automated synthesizer, as described in Van Devanter et al., *Nucleic Acids Res.* 12:6159-6168 (1984). Other methods for synthesizing oligonucleotides and polynucleotides are known in the art. Purification of oligonucleotides is by either native polyacrylamide gel electrophoresis or by anion-exchange HPLC as described in Pearson & Reanier, *J. Chrom.* 255: 137-149 (1983).

The term "recombinant" when used with reference, e.g., to a cell, or nucleic acid, protein, or vector, indicates that the cell, organism, nucleic acid, protein or vector, has been modified by the introduction of a heterologous nucleic acid or protein or the alteration of a native nucleic acid or protein, or that the cell is derived from a cell so modified. Thus, for example, recombinant cells may express genes that are not found within the native (non-recombinant or wild-type) form of the cell or express native genes that are otherwise abnormally expressed—over-expressed, under-expressed or not expressed at all.

The terms "transgenic", "transformed", "transformation", and "transfection" are similar in meaning to "recombinant". "Transformation", "transgenic", and "transfection" refer to the transfer of a polynucleotide into the genome of a host organism or into a cell. Such a transfer of polynucleotides can result in genetically stable inheritance of the polynucleotides or in the polynucleotides remaining extra-chromosomally (not integrated into the chromosome of the cell). Genetically stable inheritance may potentially require the transgenic organism or cell to be subjected for a period of time to one or more conditions which require the transcription of some or all of the transferred polynucleotide in order for the transgenic organism or cell to live and/or grow. Polynucleotides that are transformed into a cell but are not integrated into the host's chromosome remain as an expression vector within the cell. One may need to grow the cell under certain growth or environmental conditions in order for the expression vector to remain in the cell or the cell's progeny. Further, for expression to occur the organism or cell may need to be kept under certain conditions. Host organisms or cells containing the recombinant polynucleotide can be referred to as "transgenic" or "transformed" organisms or cells or simply as "transformants", as well as recombinant organisms or cells.

As used herein, the term "promoter" refers to a polynucleotide that, in its native state, is located upstream or 5' to a translational start codon of an open reading frame (or protein-coding region) and that is involved in recognition and binding of RNA polymerase and other proteins (transacting transcription factors) to initiate transcription. A promoter can be a native or non-native promoter. When the promoter sequence is not naturally operably linked to the desired polynucleotide, the promoter and/or the desired polynucleotide are considered heterologous to each other. Thus, one can refer to the promoter as a heterologous promoter or to the desired polynucleotide as a heterologous polynucleotide. When operably linked to a transcribeable heterologous polynucleotide, a promoter typically causes the transcribable heterologous polynucleotide to be transcribed in a manner that is similar to that of which the promoter is normally associated.

A genetically altered organism is any organism with any changes to its genetic material, whether in the nucleus or cytoplasm (organelle). As such, a genetically altered organism can be a recombinant or transformed organism. A genetically altered organism can also be an organism that was subjected to one or more mutagens or the progeny of an organism that was subjected to one or more mutagens and has changes in its DNA caused by the one or more mutagens, as compared to the wild-type organism (i.e, organism not subjected to the mutagens). Also, an organism that has been bred to incorporate a mutation or alteration into its genetic material is a genetically altered organism. For the purposes of this invention, the organism can be a fungi, bacteria, insect cell lines, etc.

This invention utilizes routine techniques in the field of molecular biology. Basic texts disclosing the general methods of use in this invention include Green and Sambrook, 4th ed. 2012, Cold Spring Harbor Laboratory; Kriegler, *Gene Transfer and Expression: A Laboratory Manual* (1993); and Ausubel et al., eds., *Current Protocols in Molecular Biology*, 1994—current, John Wiley & Sons. Unless otherwise noted, technical terms are used according to conventional usage. Definitions of common terms in molecular biology maybe found in e.g., Benjamin Lewin, *Genes IX*, published by Oxford University Press, 2007 (ISBN 0763740632); Krebs, et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

An "immunogenic composition" is a composition that contains an antigen where administration of the composition to an animal results in an immune response. In this invention, the antigen is a *R. microplus* immunogen which can be purified RmAQP2 (SEQ ID NO: 2, amino acids 3-293 of SEQ ID NO: 2, SEQ ID NO: 5, SEQ ID NO: 7, amino acids 3-293 of SEQ ID NO: 7, and SEQ ID NO: 9) as described herein; or which can be fragments of RmAQP2 (SEQ ID NO: 13, SEQ ID NO: 14, SEQ ID NO: 15, and SEQ ID NO: 27). The *R. microplus* immunogen can also be an expression vector which contains a heterologous promoter operably linked to a polynucleotide which encodes RmAQP2 (the polynucleotide sequence can include SEQ ID NO: 1, SEQ ID NO: 3, nucleotides 7-882 of SEQ ID NO: 3, SEQ ID NO: 4, nucleotides 7-879 of SEQ ID NO: 4, nucleotides 7-882 of SEQ ID NO: 4, SEQ ID NO: 6, SEQ ID NO: 8, and SEQ ID NO: 10), or fragments of RmAQP2 (the polynucleotide sequence can include SEQ ID NO: 24, SEQ ID NO: 25, SEQ ID NO: 26, and SEQ ID NO: 28). Because the antigen is "purified", the immunogenic compositions of this invention do not contain *R. microplus* or cells of *R. microplus*. Immunogenic compositions of this invention can contain RmAQP2, fragments thereof, or DNA encoding RmAQP2 or RmAQP2 fragments, one or more pharmaceutically acceptable diluents, pharmaceutically acceptable carriers, and/or adjuvants. Additional antigens that generate an immune response against *R. microplus* (such as RmAQP1 and/or other tick proteins) can also be included in the immunogenic compositions of this invention. The immunogenic composition of this invention may generate a humoral and/or a cellular immune response in the animal that receives the immunogenic composition. The antigen is also referred herein as an "immunogenic agent".

An "immunological response" or "immune response" to an antigen or immunogenic composition is, in an animal, the development, increase, or decrease of a humoral and/or a cellular immune response to the antigen or antigen present in the immunogenic composition. The immune response may be an increased or enhanced immune response (immuno-stimulatory) or a decrease or suppression of an immune response (immuno-suppressant). The immune response may be a systemic and/or localized immune response. For the present invention, a "humoral immune response" refers to an immune response mediated by antibody molecules, while a "cellular immune response" is one mediated by T-lymphocytes and/or other white blood cells.

In one embodiment, the fragments of RmAQP2 (SEQ ID NO: 13, SEQ ID NO: 14, SEQ ID NO: 15, and/or SEQ ID NO: 27) provide an antigenic epitope but are too small by themselves to induce an effective immune response in the ungulate. As such, the fragment of RmAQP2 may be conjugated to a suitable carrier. Suitable carriers and methods of linkage are well known in the art. Suitable carriers are typically large macromolecules such as proteins, polysaccharides, or polymeric amino acids. Non-limiting examples of carriers include bovine serum albumin, keyhole limpet hemocyanin (KLH), ovalbumin, and polylysine. One of skill in the art may use available procedures and coupling reagents to link the desired peptide to a desired carrier. For example, coupling reagents may be used to form disulfide linkages or thioether linkages from the carrier to the peptide. If the peptide lacks a disulfide group, one may be provided by the addition of a cysteine residue. Alternatively, coupling may be accomplished by activation of carboxyl groups.

"Vaccination", "vaccinate", "immunization", "immunize", and "inoculate" are synonymous and are the administration of the antigen (RmAQP2 or DNA encoding RmAQP2 described herein) or the immunogenic composition (containing RmAQP2 or DNA encoding RmAQP2) to the animal. Immunization can also include removing immunological cells from the animal, allowing such immunological cells to interact with an antigen in-vitro, and then returning those immunological cells or their progeny back to the animal's body. Exemplary routes of administration of the antigen or immunogenic composition of this invention include, but not limited to, intramuscular injection, intraperitoneal injection, subdermal injection, intradermal injection, subcutaneous injection, intravenous injection, oral administration, sublingual administration, vaginal administration, rectal administration, transmucosally, transcutaneous adsorption, intranodal administration, intracoronary administration, intraarterial administration, intratracheal administration, intraarticular administration, intraventricular administration, intracranial administration, intraspinal administration, intraocular administration, aural administration, inhalation, and intranasal administration. Vaccination and immunization involves inducing an immune response in the animal receiving the antigen or immunogenic composition.

The immunogenic agent may be prepared for administration by formulating an effective immunization dosage of the antigen with a pharmaceutically acceptable carrier or diluent, such as physiological saline or tissue culture medium. The expression "effective dosage", "effective amount", and similar phrases are that amount which will induce the production of antibodies (humoral immune response) and/or a cell-mediated immune response in an animal against the antigen, RmAQP2. Immunity is considered as having been induced in the animal when the humoral and/or cell-mediated immune response to the antigen is significantly higher than the humoral and/or cell-mediated immune response in an unvaccinated control group. In one embodiment, an immune response may be demonstrated by (i) production of antibodies against RmAQP2, (ii) a reduction in the percentage of immunized ungulates infested with *R. microplus*, (iii) a reduction in the average number of *R. microplus* on immunized ungulates, (iv) a reduction in the number of egg mass produced by *R. microplus* that feed on immunized ungulates, (v) a decrease in hatching percentages, and/or (vi) a reduction in the larvae survival after the female tick fed on an immunized ungulate, compared to the non-immunized control group. The actual effective amount or effective dose of the immunogenic composition may vary depending on (i) the formulation, (ii) the antigen, (iii) the type of immunogenic composition (e.g., protein vaccine or DNA vaccine), (iv) the age of the ungulate, (v) the size/weight/sex/breed of the ungulate, (vi) the route of administration, (vii) the time of administration, (viii) the excretion rate, and (ix) the reaction irritability. One of ordinary skill in the art can determine the appropriate dose by administering the immunogenic composition to the ungulate and assaying for an increase or, if applicable, a decrease in the immune response. An antigen dose response assay is such an assay for assessing the immune response.

In one embodiment, the suitable dosage of the immunogenic composition described herein can range from approximately 10 ng/kg/day to approximately 1 g/kg/day of the body weight of the ungulate receiving the immunogenic composition. In another embodiment, the suitable dosage of the immunogenic composition described herein can range from approximately 100 ng/kg/day to approximately 100 mg/kg/day of the body weight of the ungulate receiving the immunogenic compositions. In yet another embodiment, the suitable dosage can range from approximately 100 ng/kg/day to approximately 100 µg/kg/day of the body weight of the ungulate receiving the immunogenic composition. In yet another embodiment, the dosage can be approximately 500 ng/kg/day of the body weight of the ungulate receiving the immunogenic composition. The ungulate could be provided one dose, or alternatively two doses that are administered one or two or three weeks apart. Alternatively, the ungulate could be provided three or more doses that are administered one or two or three or more weeks apart from each other. The ungulate could also be inoculated yearly or every other year or with less frequency with the number of inoculations as previously described.

For immunogenic compositions and antigens, "treatment" refers to any of (i) the prevention of infection or reinfection, as in a traditional vaccine, (ii) the reduction or elimination of symptoms, (iii) the substantial or complete elimination of the pathogen in question, (iv) an enhanced immune response to the antigen or immunogenic composition administered to the animal, and/or (v) the reduction of a hypersensitive immune response in the animal. Treatment may be effected prophylactically (prior to infection or exposure to the antigen or infectious agent) or therapeutically (following infection or exposure to the antigen or infectious agent). Reproductive rate reduction for $R.$ $microplus$ and other ticks is also a treatment for this vaccine. Furthermore, with a reduced tick reproductive rate, the incidence of $B.$ $bovis$ infection in cattle is reduced, another "treatment". In fact, the invention described herein is useful in reducing the transmission of $B.$ $bovis$ from one bovine to another because, $R.$ $microplus$ that feed on cattle immunized with RmAQP2 will have lower reproduction rates. Thus, the number of $R.$ $microplus$ and thus the number of carriers of $B.$ $bovis$ are reduced. Other tick-borne pathogens will also have lower number of carriers and thus transmission of those diseases from cow to cow will also be reduced.

One method of assessing efficacy of an immunogenic composition involves monitoring an infection after administration of the immunogenic composition. One method of assessing efficacy of prophylactic administration of the immunogenic composition involves monitoring immune responses against the antigens in the immunogenic composition after administration of the immunogenic composition. Another method of assessing the immunogenicity of the antigens of the immunogenic composition is to express the antigens recombinantly and to screen an animal's sera or mucosal secretions by immunoblot. A positive reaction between the antigen and the animal's serum indicates that the animal previously mounted an immune response to the antigen in question--that is, the antigen is an immunogen. This method may also be used to identify immunodominant proteins and/or epitopes.

Another method involves intentionally infecting the vaccinated animal or allowing the vaccinated animal to be in the presence of infected, non-vaccinated animals and monitoring for symptoms of illness. Alternatively, one may monitor immune responses both systemically (such as monitoring the level of $IgG_1$ and $IgG_{2a}$ production) and mucosally (such as monitoring the level of IgA production) against the antigens in the immunogenic composition after administration of the immunogenic composition. Typically, serum specific antibody responses are determined post-immunization but pre-challenge, whereas mucosal specific antibody responses are determined post-immunization and post-challenge. Other techniques for monitoring the efficacy of RmAQP2 and immunogenic compositions containing RmAQP2 are described in the examples, below. In these methods, one can assess the weight of the eggs laid after feeding, the hatching rate of tick eggs, and the survival rate for the tick larvae. Lower reproduction of $R.$ $microplus$ and other ticks is indicative that the RmAQP2 antigen and immunogenic compositions containing RmAQP2 are effective.

Immunogenic compositions of the present invention may be used either alone or in combination with other antigens and/or optionally with one or more immunoregulatory agents ("adjuvants"). Non-limiting examples of adjuvants include saponin, mineral oil, vegetable oil, oil-in-water emulsion, water-in-oil emulsion, water-in-oil-in-water emulsion, aluminum hydroxide, aluminum phosphate, squalene and squalene-like compounds, Freund's complete adjuvant, Freund's incomplete adjuvant, muramyl dipeptide, monophosphoryl lipid A, polyphosphazine, $E.$ $coli$ LT (or LT-B, native or toxoid), $Vibrio$ $cholera$ toxin (CTX or CT), CpG motif containing oligonucleotide, and compounds that interact with Toll-like Receptors (TLR).

The immunogenic composition of this invention may contain one or more pharmaceutically acceptable carriers. Non-limited examples of such pharmaceutically acceptable carriers include phosphate buffered saline (PBS), lactose, dextrose, sucrose, sorbitol, mannitol, starch, acacia gum, calcium phosphate, calcium silicate, water, syrup, methyl hydroxybenzoate, propyl hydroxybenzoate, talc, stearic acid, magnesium, mineral oil, and polymers such as alginate, gelatin, microcrystalline cellulose, methyl cellulose, cellulose, polyvinylpyrrolidone, poly-lactic acid (PLA), poly-glycolic acid (PGA), and poly-lactic-co-glycolic acid (PLGA). In addition to the above ingredients of the pharmaceutical composition according to the present invention may further comprise lubricants, wetting agents, sweetening agents, flavoring agents, emulsifiers, suspending agents, preservatives, etc. Suitable pharmaceutically acceptable carriers and formulations are described in detail in $Remington's$ $Pharmaceutical$ $Sciences$ (19th ed., 1995). While the immunogenic compositions of the present invention can be used in animals but not humans, "pharmaceutically acceptable" refers to those items, compounds, etc. that are approved for use in human and/or in animals. In one embodiment, live or dead $R.$ $microplus$ are not pharmaceutically acceptable carriers nor adjuvants for this invention. In another embodiment, live or dead $B.$ $bovis$ are not pharmaceutically acceptable carriers nor adjuvants for this invention.

The invention also provides for the immunogenic composition described herein to be used as a medicament. A medicament is preferably able to generate an immune response in an animal. The invention also provides for the use of the immunogenic composition of the invention in the manufacture of a medicament for generating an immune response in an animal. In one embodiment, the medicament is a vaccine or an immunostimulatory composition or an immunosuppressant composition.

The invention provides methods for inducing or increasing an immune response using the immunogenic composition. The immune response is preferably protective and can include antibodies and/or cell-mediated immunity (including systemic and mucosal immunity). Immune responses include booster responses. The invention also provides methods for suppressing or decreasing an immune response in the animal to the antigen using an immunogenic composition. Such a suppression of an immune response may be useful if the animal is hypersensitive to the antigen.

A prophylactic antigen or prophylactic immunogenic composition can be administered to the animal, especially to young animals, to pregnant animals, and to elderly animals. The age of the young animal will vary depending on the animal's lifespan and if the young has maternal antibodies upon birth or, if the animal is a mammal, obtains maternal antibodies during nursing. Administering a prophylactic immunogenic composition to a pregnant animal may help stimulate the immune response of the fetus or baby animal prior to and shortly after birth. It may also stimulate the pregnant animal's immune system thereby improving the pregnant animal's health. Of course, administering prophylactic compositions to an elderly animal may boost the elderly animal's immune system to the antigen contained with the composition and thus help prevent the elderly animal from being infected with the bacteria, virus, or parasite containing the antigen. Administering an immunosuppressant composition would be considered a prophylactic administration in that one desires to reduce the animal's response to the antigen contained in the immunosuppressant composition prior to the animal's next exposure to the antigen.

The invention also includes kits containing one or more containers of the immunogenic compositions and/or antigens of the invention. The immunogenic composition can be in liquid form or can be lyophilized; as can be the antigens. Suitable containers for the immunogenic compositions and/or antigens include, for example, bottles, jugs, vials, syringes, and test tubes. Containers can be formed from a variety of materials, including glass or plastic. A container may have a sterile access port (for example, the container may be an intravenous solution bag or a vial having a stopper pierceable by a hypodermic injection needle). The kit can also contain a second container inside of which is a pharmaceutically acceptable carrier, such as phosphate buffered saline (PBS), Ringer's solution, or dextrose solution. The kit can also contain other materials useful to the end-user, including other pharmaceutically acceptable formulating solutions such as buffers and/or diluents, filters, needles, and syringes or other delivery devices. The kit may optionally include an adjuvant in a container. The kit can also contain written instructions for administering the immunogenic composition and/or antigen and other contents of the kits to subjects. The written instructions may describe methods for inducing an immune reaction or methods for treating infections. The invention also includes a delivery device pre-filled with the immunogenic composition of the invention.

The terms "approximately" and "about" refers to a quantity, level, value or amount that varies by as much as 30% in one embodiment, or in another embodiment by as much as 20%, and in a third embodiment by as much as 10% to a reference quantity, level, value or amount. As used herein, the singular form "a", "an", and "the" include plural references unless the context clearly dictates otherwise. For example, the term "a bacterium" includes both a single bacterium and a plurality of bacteria.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation. All documents cited herein are incorporated by reference.

EXAMPLE 1

In Silico Sequence Analysis of the *R. microplus* AQP2

As discussed in Guerrero, et al., *Insect Biochem. Mol. Bio.* 35:585-595 (2005), a cDNA library was generated from *R. microplus* mRNA, and various cDNA clones were sequenced and annotated as part of the *R. microplus* gene index project. One cDNA sequence encodes RmAQP2 (Guerrero, et al., (2014)). Multiple alignments of amino acid sequences are generated using the Multiple Alignment Module of LaserGene (DNASTAR, Inc. Madison, Wis.). The Simple Modular Architecture Research Tool (SMART) (EMBL, Heidelberg, Germany) and the Transmembrane Hidden Markov Model package 2 (TMHMM2) Center for Biological Sequence Analysis, Technical University of Denmark, Lyngby, Denmark) are used to predict domains and signal peptides in the RmAQP2 protein sequence. The tool Transmembrane Protein Representation in 2 Dimensions (TMRPres2) (Spyropoulos, et al., *Bioinformatics* 20:3258-3260 (2004)) is used to create visual representation of the RmAQP2 protein for topology analyses. See FIG. 1.

Multiple alignment analysis reveal that the RmAQP2 amino acid sequence (SEQ ID NO: 1) presents 41.2%, 86.0%, 53.0%, 53.5%, 54.1%, and 65.5% identity to *R. microplus* AQP1 (GenBank ID: KJ626366.1), *Dermacentor variabilis* AQP9 (GenBank ID: ABI53034.1), *R. sanguineus* AQP1 (GenBank ID: CAR66115.1), *Ixodes ricinus* AQP1 (GenBank ID: CAX48964.1), *I. scapularis* AQP1 (GenBank ID: XP_002399532.1) and *I. scapularis* AQP2 (GenBank ID: XP_002400655.1), respectively. See, Guerrero, et al. (2014). Considering domain organization, RmAQP2 contains two AQP signature NPA motifs in the sequence; the same number of NPA motifs possessed by the previously mentioned AQPs, except for *I. scapularis* AQP2. The two AQP NPA motifs are present in RmAQP2 at the amino acid positions 84 to 86 and 216 to 218. Topology prediction indicates that RmAQP2 has six transmembrane-spanning regions and five loops; two loops are intracellular while the remaining three loops are extracellular. See FIG. 1. Therefore, the topology prediction of RmAQP2 is consistent with predicted topology for other members of the AQP family. See, Borgnia, et al. (1999); Gonen and Walz (2006); and Campbell, et al. (2008). This model also predicts the localization of the N- and C-terminal ends of RmAQP2 on the cytoplasmic side of the plasma membrane, a characteristic feature of most known AQP proteins.

EXAMPLE 2

RmAQP2 Transcription Pattern in Tissue and Live Stages of the Tick

The transcription level of RmAQP2 is investigated by quantitative real-time PCR (RT-qPCR) in different tissues and stages of R. microplus fed on uninfected calves (B. bovis—free calves).

Two Holstein calves, ages 3 to 4 months, test negative for B. bovis using a PCR protocol described by Bastos, et al. (Parasites & Vectors 2:57 (2009)) and a cELISA protocol described by Goff, et al. (Clin. Vaccine Immunol. 13:1212-1216 (2006)). The animals are maintained according to protocols approved by the University of Idaho Institutional Animal Care and Use Committee. To obtain unfed adult ticks, approximately 40,000 larvae from 2 grams of eggs of R. microplus La Minita strain (Stiller, et al., J. Med. Entomol. 39:667-670 (2002)) are placed under a cloth patch on the uninfected calves. On day 13-14, engorged nymphs are manually removed and held in an incubator at 25° C. with 96% relative humidity (RH) to molt to adults. After 2-3 days of incubation, freshly molted unfed adult females and males are sorted out and are used for evaluation of gene expression.

Because several reference gene candidates from different tissues and stages of R. microplus were determined to be inadequate for gene expression normalization, the expression level of RmAQP2 is normalized to the total amount of RNA used to generate the cDNA and the transcription level is calculated as a relative expression using the highest or lowest Cq value for RmAQP2 in a given sample as a control. See, Bastos, et al. (2009) and infra. To evaluate gene expression, six biological replicates of unfed larvae (approximately 100 larvae per sample), engorged nymphs (10 nymphs per sample), unfed males (10 males per sample), and individual salivary glands, ovaries and guts of partially engorged females (at day 5 of feeding) are analyzed by RT-qPCR.

In order to make solid significant observations regarding gene expression, qPCR is performed using the pertinent requirements of the minimum information for publication of qPCR experiments. See, Bustin, et al. (Clin. Chem. 55(4): 611-22 (2009)). Unfed larvae, engorged nymphs, unfed male ticks, and salivary glands, guts and ovaries from partially engorged tick females are collected in RNAlater® (Ambion, Thermo Fisher Scientific, Waltham, Mass.) and stored at −20° C. following the manufacturer's recommended protocol. Total RNA is extracted using the RNAqueous® Kit (Ambion, Thermo Fisher Scientific, Waltham, Mass.) according to the manufacturer's recommended protocol and quantified by Qubit® fluorometer (Thermo Fisher Scientific, Waltham, Mass.). Two hundred nanograms of total RNA are utilized for cDNA synthesis using the Superscript® Vilo™ cDNA Synthesis Kit (Thermo Fisher Scientific, Waltham, Mass.) following the manufacturer's recommended protocol. Technical replicates are performed to evaluate enzymatic variations during the synthesis of cDNA in a given RNA sample. The RmAQP2 cDNA sequence (SEQ ID NO: 1) is used to design qPCR primers to amplify a 105 bp fragment spanning nucleotides 349 to 453 in SEQ ID NO: 1. The qPCR forward primer is 5'-gtaagtcaccgcacagta-3' (SEQ ID NO: 11) and the reverse primer is 5'-tacacaatagcgaggtt-3' (SEQ ID NO: 12).

Quantitative real-time PCR is performed in a CFX96™ Real-Time PCR Detection System using the SsoFast™ EvaGreen® Supermix (Bio-Rad, Hercules, Calif.). Cycling conditions consist of an enzyme activation step of 95° C. for 30 seconds followed by 40 cycles of 95° C. denaturation for 5 seconds and annealing/extension of 60° C. for 5 seconds. Reactions are performed in duplicate in 20 µl using 200 nM of each primer and 2 µl of a 1/20 dilution of cDNA (made above) as template. The CFX Manager™ Software (Bio-Rad, Hercules, Calif.) is used to analyze the RT-qPCR data. After normalizing gene expression to the total amount of RNA used to generate the cDNA, the RmAQP2 transcription level is calculated as a relative expression using the formula: Relative expression$_{(sample)}$=2$^{[Cq(control)-Cq(sample)]}$, where the control is either the highest or lowest Cq value for the gene of interest (Bastos, et al. (2009); and Bastos, et al., PLOSONE 8:e67765 (2013)). Melt curve analyses show the absence of primer dimers and nonspecific amplification. The absence of PCR product in no RNA control reactions and in no transcriptase reverse control reactions indicate the specificity of the RmAQP2 RT-qPCR.

Figure 2:
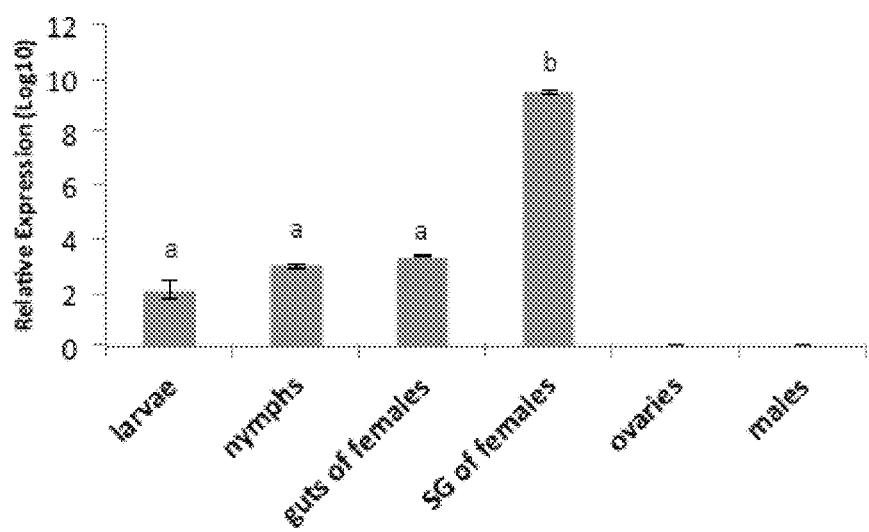
FIG. 2 illustrates the relative expression of RmAQP2 in unfed larvae, engorged nymphs, unfed males, and salivary glands, gut and ovaries of R. microplus females. Different letters (a, b) above the bars indicate significant statistical differences (one-way ANOVA, Tukey post hoc test, $P<0.001$).

Relative levels of expression of RmAQP2 are different in larvae (2.5[±0.66]), nymphs (3.0[±0.23]), female guts (3.3 [±0.99]) and female salivary glands (9.5 [±1.73]). See FIG. 2. However, no transcripts are detected in ovaries of partially engorged females and unfed male ticks. The relative gene expression of RmAQP2 in the female salivary glands samples is approximately 6 times higher (P<0.001) than in larvae, nymphs and guts of females.

EXAMPLE 3

RmAQP2 Expression in Different Tick Stages and Tissues using Immunoblot Assays

Following the detection of RmAQP2 mRNA in unfed larvae, engorged nymphs, and guts and salivary glands of partially engorged females, the presence of RmAQP2 in these tick stages and tissues is examined using immunoblot assays.

Based on the predicted topology of RmAQP2, three synthetic peptides from the predicted extracellular loops of RmAQP2 are manufactured by BioSynthesis, Inc. (Lewisville, Tex. (FIG. 1). The amino acid sequence of Peptide 1, which is a 10-mer, is LGSVGLAAAP (SEQ ID NO: 13) and covers amino acids 52-61, inclusive, of RmAQP2. The DNA sequence encoding Peptide 1 is in SEQ ID NO: 24. The amino acid sequence of Peptide 2, which is a 32-mer, is ADALSQVDVNLAIVYGTNATAPVFSCFPAPGV (SEQ ID NO: 14) and covers amino acids 125-156, inclusive, of RmAQP2. The DNA sequence encoding Peptide 2 is in SEQ ID NO: 25. The amino acid sequence of Peptide 3, which is a 19-mer, is MCGWGSAVFSFRSYNWFWV (SEQ ID NO: 15) and covers amino acids 229-247 of RmAQP2. The DNA sequence encoding Peptide 3 is in SEQ ID NO: 26. Three six-week-old BALB/c female mice are immunized subcutaneously with 50 mg of a composition containing Peptides 1, 2, and 3 together, diluted in 0.1 ml of sterile PBS and emulsified with an equal volume of TiterMax® Gold Adjuvant (Sigma-Aldrich, St. Louis, Mo.). The primary immune response is boosted twice by subcutaneous immunization at 15-day intervals with the same concentration of peptide antigen plus adjuvant. Mice immune response is monitored by ELISA by standard procedures using the RmAQP2 peptides (Peptides 1, 2, or 3) as antigens. Three days prior to cell fusion, mice are immunized intravenously with the same concentration of antigen without adjuvant. Cell fusions and cloning by limiting dilution are performed by standard procedures described in Yokoyama, W M (*Production of monoclonal antibodies*, pp. 2.5.1-2.5.17 in *Current Protocols in Immunology Vol.* 1, ed.: Coligan, Wiley Intersciences Inc. (New York, N.Y.) (1994)). Supernatants from the initial fusion and from clones obtained by limiting dilution are screened by ELISA. A total of 10 hybridoma clones are obtained, and the hybridoma supernatants are used to assess the expression of RmAQP2 in tick tissues and stages by immunoblot.

For the immunoblot, total proteins are prepared from unfed larvae, engorged nymphs, and salivary glands and guts of partially engorged females (at 5 days of feeding). Tick tissues and stages are suspended in lysis buffer, Nonidet-P40 (NP-40) (150 mM sodium chloride 1.0% NP-40, 50 mM Tris, pH 8.0) and protease inhibitor (1 µg/ml) and are homogenized. Total protein is quantified by Micro BCA Protein Assay (Thermo Fisher Scientific, Waltham, Mass.) using manufacturer's recommended protocol, and 3 µg of total protein are separated into 4-20% Mini-PROTEAN® TGX™ Precast Gels (Bio-Rad, Hercules, Calif.) under reducing conditions. Proteins are transferred to a nitrocellulose membrane (Whatman, Ltd., Piscataway, N.J.) for 1 hour at 100 V. Each membrane is blocked with 5% skim milk in TBS (Tris-buffered saline: 25 mmol/L Tris-HCl, 150 mmol/L NaCl, pH 7.6) for 1 hour at room temperature, are washed three times in TBS, and are incubated for 1 hour with the primary antibody which, for this immunoblot assay, is hybridoma supernatant 147-677.13.11 at a 1:3 dilution. The membrane is then washed three times with TBS and is incubated for 30 minutes with goat anti-mouse HRP conjugated secondary antibody (KPL, Gaithersburg, Md.) at a 1:5,000 dilution. After incubation, the membrane is washed again three times with TBS and is developed using HyGlo Quick Spray chemiluminescent HRP antibody detection reagents (Denville Scientific, Metuchen, N.J.) using manufacturer's recommended protocol. Anti-Bm86 polyclonal antibody is used as previously described in Laughery, et al. (PLOSONE 9:e97890 (2014)) as a positive control to demonstrate the presence of tick antigens in tick gut tissues for the immunoblot assays.

The RmAQP2 antibodies bound to a protein of approximately 50 KDa (the predicted molecular weight of RmAQP2) only in the gel containing proteins isolated from salivary glands of partially engorged females. Interestingly, the RmAQP2antibodies failed to bind to proteins isolated from larvae, nymphs or guts of partially engorged females.

EXAMPLE 4

Silencing RmAQP2 in Salivary Glands and its Effect on Protein Expression

In order to assess the impact of silencing of RmAQP2 expression, and thus the absence of the protein, on the tick, double stranded RNA (dsRNA) is synthesized using the protocols described in Bastos, et al. (2009) and Bastos, et al., *Parasites & Vectors* 3(1):111 (2010). To make the DNA template for synthesis of the dsRNA to be used in the silencing (described in the paragraph below) two sets of primers are designed based on the cDNA sequence of RmAQP2 (SEQ ID NO: 1). The first set of primers are located toward the 5' end of the gene (from nucleotide 17 to nucleotide 414) and generates an amplicon of 397 bp, with the forward primer having the sequence 5'-aattcagcagcaggagaagc-3' (SEQ ID NO: 16) and the reverse primer having the sequence 5'-cggcgtacaccaggtaaact-3'(SEQ ID NO: 17). The sequence of this amplicon is in SEQ ID NO: 18. When used to generate dsRNA as described below, the nucleotide sequence of the forward strand of the dsRNA is in SEQ ID NO: 19. The reverse strand of the dsRNA has a sequence that is the reverse complement of SEQ ID NO: 19. The second set of primers are located toward the 3' end of the gene (from nucleotide 614 to nucleotide 1009) and generates an amplicon of 396 bp, with the forward primer having the sequence 5'-cctctcctcgtcggcctca-3' (SEQ ID NO: 20) and the reverse primer having the sequence 5'-cggctaaaacgcaaaaaggt-3' (SEQ ID NO: 21). The amplicon's sequence is in SEQ ID NO: 22, and the nucleotide sequence of the forward strand of the dsRNA generated below using this amplicon is in SEQ ID NO: 23. The reverse strand of the dsRNA has a sequence that is the reverse complement of SEQ ID NO: 23. The protocols described in Bastos, et al. (2009) and Bastos, et al., *Parasites & Vectors* 3(1):111 (2010) are used to generate these dsRNA. Blast analysis of the two DNA sequences generated using these sets of primers does not reveal significant homology to any known tick DNA sequence other than RmAQP2. Not wishing to be bound to a particular hypothesis, it is believed that the dsRNA generated from these sequences does not interfere with any other gene's expression and/or translation in *R. microplus*.

To make the two dsRNA (SEQ ID NO: 19 and SEQ ID NO: 23), each amplicon (SEQ ID NO: 18 and SEQ ID NO: 22) is individually ligated into pCR® II-TOPO® (Thermo-Fisher Scientific, Waltham, Mass.) using the manufacturer's recommended protocol. The ligated plasmids are sequenced and are used for in-vitro transcription. The MEGAscript® Transcription Kit (Ambion, Waltham, Mass.) is used for the dsRNA synthesis following the manufacturer's recommended protocol in which dsRNA is produced directly (without an annealing step) from the DNA template using the T7 promoters already present in the plasmid. The two RmAQP2 dsRNA molecules are checked by electrophoresis on agarose gel, are quantified by spectrophotometry, and are stored at −20° C. until used for tick injection.

For this assessment of the RmAQP2 activity in ticks fed on a *Babesia bovis* infected calf, naive calves are infected with approximately $1.4 \times 10^8$ *B. bovis*-infected erythrocytes (T2Bo strain) (Goff, et al., *Ann. N.Y. Acad. Sci.* 849:161-180 (1998)). The infected calves are monitored daily for the presence of *B. bovis* in peripheral blood and clinical signs of babesiosis. Parasitemia of *B. bovis* in peripheral blood is examined by qPCR to amplify the single copy msa-1 gene using the protocol described in Bastos, et al. (2009). The *B. bovis*-infected animal presented clinical indications of acute *B. bovis* infection including a drop in packed cell volume (PCV), fever and detection of parasites in peripheral blood by qPCR.

In one experiment, one group of 200 female ticks are injected with a single dsRNA fragment (SEQ ID NO: 19) as the experimental group, and 200 female ticks are injected with EDTA buffer as the negative control. Both of these groups of female ticks are fed on a calf infected with *B. bovis*. In a second experiment, one group of 200 female ticks are injected with both dsRNA fragments (SEQ ID NO: 19 and SEQ ID NO: 23) as the experimental group and one group of 200 female ticks are injected with EDTA buffer as the negative control. Both of these groups of ticks are fed on an uninfected calf. For both experiments, individual female ticks are injected with 1 µl dsRNA (for a total of approximately $1 \times 10^{11}$ molecules dissolved in 0.1 mM EDTA) or buffer (0.1 mM EDTA) through the coxal membrane at the base of the 4th leg on the right ventral side using the protocol described in Bastos, et al. (2009). Ticks in the second experiment that are injected with both dsRNA segments (SEQ ID NO: 19 and SEQ ID NO: 23) receive $0.5 \times 10^{10}$ of each dsRNA molecule, for a total of $1 \times 10^{11}$ molecules. Injections are accomplished using a 10 µl syringe with a 33 gauge needle (Hamilton, Bonaduz, Switzerland) and the microprocessor controlled UMP3 injection pump apparatus (World Precision Instruments, Berlin, Germany). After the injection, the dsRNA-injected females, plus an equal number of males, and the buffer-injected females, plus an equal number of males, are placed under individual stockinet sleeves to feed on either an uninfected calf or a *B. bovis*-infected calf. Male ticks are necessary to insure that the female ticks mate and will feed to repletion. Silencing level of RmAQP2 is determined using RT-qPCR as described above. Five days after the dsRNA injection, 20 partially engorged female ticks from each group are collected for dissection. Tissue collection, extraction of total RNA, cDNA synthesis, and qPCR are performed as described above. A total of 6 biological replicates are analyzed at day 5 after the dsRNA injection.

Figure 3A:
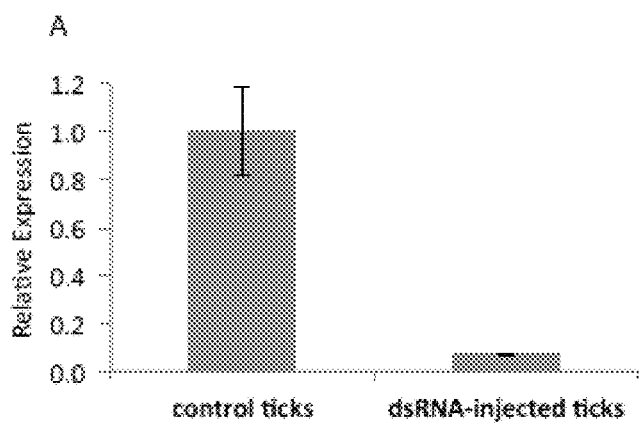
FIG. 3A and FIG. 3B show the relative transcript level of RmAQP2 in salivary glands of partially engorged R. microplus females injected with dsRNA or buffer (negative control).
Figure 3B:
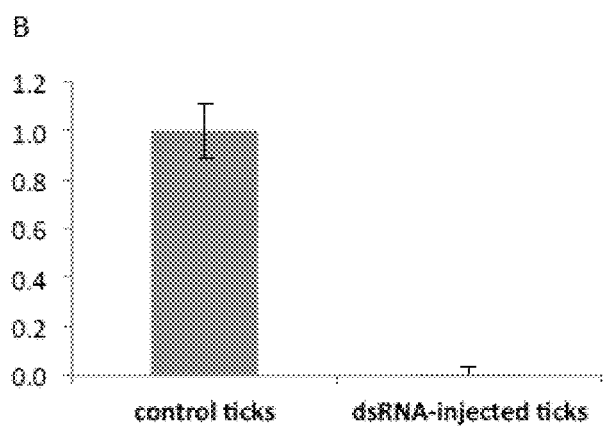

Similar levels of gene silencing are obtained by injecting ticks with either one (experiment 1) or two (experiment 2) dsRNA fragments. RmAQP2 is silenced 92.8% (±0.26%) and 99.3% (±3.70%) in ticks injected with one dsRNA or two dsRNA fragments, respectively. See FIG. 3A and FIG. 3B.

Next, the effect of RmAQP2 silencing on protein expression in salivary glands is examined. Female ticks from experiment 2 that are injected with both the 396 bp dsRNA fragment and the 397 bp fragment ($0.5 \times 10^{10}$ of each dsRNA molecule for a total of $1 \times 10^{11}$ molecules of dsRNA dissolved in 0.1 mM EDTA) are fed on an uninfected calf for 5 days. An equal number of female ticks are injected with 0.1 mM EDTA as negative control. The ticks are then dissected, and individual salivary glands are collected. Proteins are isolated as described above and run on an agrose gel for immunoblotting using the hybridoma antibodies specific for RmAQP2 produced as described above. No RmAQP2 protein is detected in salivary glands of dsRNA-injected ticks. A protein having molecular weight of approximately 50 kDa (the predicted molecular weight of RmAQP2) is detected in salivary glands of the negative control non-silenced ticks. For this immunoblot assay, hybridoma supernatant 147-677.13.11 at a 1:3 dilution is used. Anti-mouse HRP conjugate is used at a 1:5,000 dilution. Assays are developed using chemiluminescent HRP detection reagents as described above. Collectively, this data demonstrates gene silencing and abrogation of protein expression as a consequence of injecting ticks with dsRNA identical to portions of the RmAQP2 gene.

EXAMPLE 5

Effect of RmAQP2 Silencing on Tick Fitness

Two independent experiments are performed to investigate the in-vivo biological effect of RmAQP2 silencing. For the first experiment, adult female ticks are injected with one segment of dsRNA from the 5' end of the gene (from nucleotide 17 to nucleotide 414 (SEQ ID NO: 19)) described above and are fed on *B. bovis*-infected calf. For the second experiment, adult female ticks are injected with two dsRNA fragments (397 bp (SEQ ID NO: 19) and 396 bp (SEQ ID NO: 23)) described above and are fed to repletion on an uninfected calf (*B. bovis*-free animal). For the second experiment, adult female ticks are injected with one segment of dsRNA from the 5' end of the gene (from nucleotide 17 to nucleotide 414 (SEQ ID NO: 19)) and are fed on *B. bovis*-infected calf. The protocol details for injections and feeding on the calves are described in Example 4 above.

After injection, the ticks (male and female; experimental and negative control as described above) are placed under individual stockinet sleeves to feed on either an uninfected calf or a *B. bovis*-infected calf. Individual stockinet sleeves are checked daily for the presence of engorged female ticks. Fully engorged females are collected, weighed, and put in individual wells in 24-well plates at 26° C. for oviposition. At day 14 after the beginning of oviposition, egg masses laid by each individual female are weighed and put in individual vials to evaluate hatching. Hatching is evaluated at 30 days after the egg masses are weighed, and hatching positive is defined as the presence of any larvae from eggs of an individual female. The larval progeny are maintained in individual vials at 26° C. for 45 days, and the larval survival is determined as the presence of any live larvae in larval progeny from individual females.

In both experiments, the percentage of engorged females, weight of engorged females, oviposition rate, egg masses, percentage of hatching and percentage of larvae survival are evaluated (see Table 4 (experiment 1: ticks injected with one dsRNA strand (397 bp, SEQ ID NO: 19) feeding on infected calf) and Table 5 (experiment 2: ticks injected with both dsRNA strands (397 bp, SEQ ID NO: 19 and 396 bp, SEQ ID NO: 23) feeding on uninfected calf)).

For the ticks that fed on a calf during acute *B. bovis* infection (experiment 1), identical numbers of females from both groups (the RmAQP2 silenced group (injected with only 397 bp dsRNA, SEQ ID NO: 19) and negative control group), feed to repletion. The average weight of the RmAQP2 silenced group engorged females is 361.8 mg and is significantly higher (P<0.05) than the negative control group (342.4 mg). This result suggests that silencing the aquaporin gene prevents the removal of excess water from the blood meal. Silencing of RmAQP2 has no effect on the percentage of oviposition and weight of egg masses. In contrast, only 50% of the egg masses hatched in the RmAQP2 silenced group compared to 90.2% hatching rate in the negative control group. Surprising and unexpectedly, none of the larvae survived in the RmAQP2 silenced group compared to 100% larvae survival in the negative control group (Table 4).

TABLE 4

| Female ticks on an infected calf | Percentage of engorged females | Weight (mg) of engorged females | Oviposition rate | Egg mass (mg) | Percentage of hatching | Percentage of larvae survival |
|---|---|---|---|---|---|---|
| Negative control | 46.1% (83/180) | 342.4 (±5.6) | 98.7% (82/83) | 141.1 (±42.3) | 90.2% | 100% |
| RmAQP2 silenced | 46.1% (83/180) | 361.8 (±7.0)[1] | 96.3% (80/83) | 139.5 (±50.5) | 50.0%[2] | 0% |

[1] t test ($P < 0.05$)
[2] Chi-squared test ($P < 0.05$)

For the ticks that feed on the uninfected calf (experiment 2 in which the experimental group of ticks are injected with both dsRNA fragments (397 bp, SEQ ID NO: 19 and 396 bp, SEQ ID NO: 23)), similar numbers of females from both groups (the RmAQP2 silenced group and negative control group) survive and feed to repletion. The average weight of engorged females in the RmAQP2 silenced group is 323.3 mg and is significantly higher (P<0.05) than the average weight of engorged females in the negative control group (305.6 mg). Oviposition rate is not affected by RmAQP2 silencing; however, egg mass weight is significantly lower (P<0.05) in the RmAQP2 silenced group (134.7 mg) than in the negative control group (203.4 mg). Higher replete weight in combination with reduced egg mass weight suggests the larger blood meal contained less protein, the result that would be expected to result from silencing of the aquaporin gene in the tick that is responsible for removing excess water from the blood meal. Interestingly, the percentage of hatching is significantly reduced (P<0.05) in the RmAQP2 silenced group (81.2%) compared to the negative control group (97.7%). However, 100% of the larvae survive in both the RmAQP2 silenced group and negative control group (see Table 5).

TABLE 5

| Female ticks on an uninfected calf | Percentage of engorged females | Weight (mg) of engorged females | Oviposition rate | Egg mass (mg) | Percentage of hatching | Percentage of larvae survival |
|---|---|---|---|---|---|---|
| Negative control | 37.7% (68/180) | 305.6 (±6.1) | 98.5% (67/68) | 203.4 (±39.0) | 97.7% | 100% |
| RmAQP2 silenced | 51.1% (92/180) | 323.3[1] (±5.7) | 94.5% (87/92) | 134.7[1] (±63.6) | 81.2%[2] | 100% |

[1] t test ($P < 0.05$)
[2] Chi-squared test ($P < 0.05$)

EXAMPLE 6

Production and Purification of Recombinant RmAQP2

RmAQP2 cDNA (SEQ ID NO: 1) is optimized for expression in *Pichia pastoris;* and the optimized nucleotide sequence is in SEQ ID NO: 4. This optimized DNA sequence is then modified to contain an EcoR1 restriction sequence at the 5' end and Not1 restriction sequence at the 3' end to generate the nucleotide sequence in SEQ ID NO: 6 (optimized EcoR1-RmAQP2-Not1) which has an open reading frame which is translated into the amino acid sequence of SEQ ID NO: 7. Optimized EcoR1-RmAQP2-Not1 is cloned into pPIC expression vector (described below) to yield pPICRmAQP2. The open reading frame encoding RmAQP2 in pPICRmAQP2 has the DNA sequence of SEQ ID NO: 8 and yields RmAQP2 linked to a HIS tag (see SEQ ID NO: 9). The degenerate polynucleotide sequence for RmAQP2 is in SEQ ID NO: 10. cDNA is prepared for ligation by restriction enzyme digestion reactions with EcoR1 (New England Biolabs, Ipswich, Mass.) and Not1 (New England Biolabs, Ipswich, Mass.) using manufacturer's recommended protocol. The EasySelect *Pichia* Expression Vectors (Thermo Fisher Scientific, Waltham, Mass.), pPIC is also digested with these restriction enzymes and is purified by agarose gel electrophoresis followed by gel extraction. Digested RmAQP2 is ligated into pPIC-digested vector using the TA Cloning Kit (Thermo Fisher Scientific, Waltham, Mass.) with T4 DNA ligase [1 unit/µL] (Thermo Fisher Scientific, Waltham, Mass.) using a modified version of the TA Cloning Kit protocol. A 10 µl ligation reaction containing 1× T4 DNA ligase reaction buffer, 137 ng RmAQP2 cDNA, 50 ng pPICdigested vector, and 1 µl T4 DNA ligase is incubated for 17 hours at 4° C. to generate pPICRmAQP2.

OneShot TOP10® *E. coli* (Thermo Fisher Scientific, Waltham, Mass.) are transformed with ligation reaction (pPICRmAQP2) and plated on low salt LB agar (1% tryptone, 0.5% yeast extract, 0.5% sodium chloride, 1.5% agar) with 25 µg/ml ZEOCIN (Thermo Fisher Scientific, Waltham, Mass.). Resulting colonies are screened, via PCR, using vector primers 5'AOX1 and 3' AOX1 and DNA isolated from positive colonies using the QIAprep Spin Miniprep Kit (Qiagen, Gaithersburg, Md.) according to manufacturer's recommended protocols. The sequence of both strands of putative positive clones is verified by DNA sequencing.

Ten µg of pPICRmAQP2 is digested with Sst1 (Thermo Fisher Scientific, Waltham, Mass.) to linearize the expression vector per recommendation of the EasySelect *Pichia* Expression Kit protocol (Thermo Fisher Scientific, Waltham, Mass.). A freshly prepared 80 µl aliquot of electrocompetent *P. pastoris* KM71H strain and 5 µg linearized pPICRmAQP2 DNA is used for transformations according to the manufacturer's recommended protocol using the Bio-Rad Gene Pulser and Pulse Controller with pulse settings of 1.5 kV, 200 Ω and 25 µFD (Hercules, Calif.). Transformation mixtures are plated on YPDS (1% yeast extract, 2% peptone, 2% dextrose, 1M sorbitol, 2% agar) plates containing 100 µg/ml ZEOCIN and are incubated at 30° C. for four days to allow colonies to develop.

Direct screening of individual *Pichia* KM71H colonies using PCR is performed by modifying the direct screening protocol from Linder et al. (*BioTechniques* 20:980-982 (1996)) and the EasySelect *Pichia* Expression Kit manual. Single colonies are prepared as described in the direct screening protocol and 2.5 µl is used in a 25 µl PCR including 10 mM Tris (hydroxymethyl) aminomethane hydrochloride, pH=8.3, 50 mM KCl, 2.5 mM $MgCl_2$, 0.05 mM each dNTP, 2 µM 5' AOX1 vector primer, 2 µM 3' AOX1 vector primer, 0.16 µL of a 1 vol:1 vol mix of AmpliTaq DNA polymerase (5 U/µl stock; Thermo Fisher Scientific, Waltham, Mass.) and TaqStart antibody (1.1 µg/µl stock; Clontech, Mountain View, Calif.). The cycling profile includes a 95° C. for 5 minutes initial denaturation step, thirty cycles of 95° C. for 1 minute, 54° C. for 1 minute, 72° C. for 1 minute and a final extension at 72° C. for 7 minutes. RmAQP2-positive colonies produce an approximately 1070 bp band. The *Pichia* KM71H colonies are also screened using gene specific primers for RmAQP2 as a control.

Small-scale expression experiments are used to determine the optimal method and conditions for the expression of recombinant RmAQP2. These experiments used protocols similar to the protocols described in the EasySelect *Pichia* Expression Kit manual using 3 mL cultures grown in BMGY (1% yeast extract, 2% peptone, 100 mM potassium phosphate pH 6.0, 1.34% yeast nitrogen base with ammonium sulfate without amino acids, $4 \times 10^{-5}$% biotin, 1% glycerol) and BMMY media (1% yeast extract, 2% peptone, 100 mM potassium phosphate pH 6.0, 1.34% yeast nitrogen base with ammonium sulfate without amino acids, $4 \times 10^{-5}$% biotin, 0.5% methanol). Cultures are replenished to 0.5% final methanol concentration every 24 hours.

Both the intracellular cell pellets and the secreted supernatant samples are analyzed by denaturing gel electrophoresis under reducing conditions using the NUPAGE Electrophoresis System (Thermo Fisher Scientific, Waltham, Mass.) and NUPAGE 4-12% Bis-Tris gels (Thermo Fisher Scientific, Waltham, Mass.) in the XCell SURELOCK Mini-Cell (Thermo Fisher Scientific, Waltham, Mass.) with 1× NUPAGE MOPS SDS Running Buffer (Thermo Fisher Scientific, Waltham, Mass.) according to manufacturer's recommended protocols. Proteins are visualized by staining with Coomassie Brilliant Blue R-250 using a modified Fairbank's method (Wong, et al., *Biotechniques* 28:426-432 (2000)). Recombinant RmAQP2 is localized in the cell pellet sample.

Next, large scale cultures are grown to produce larger quantities of recombinant RmAQP2. Cells are grown in 25 mL BMGY media in 500 ml baffled flasks in a shaking incubator (275 rpm) at 29° C. to an $OD_{600}$=2-6. Cells are harvested by centrifugation and are resuspended in BMMH to an $OD_{600}$=1. The resuspended cells are returned to the incubator at 29° C. with shaking to induce expression. Every 24 hours, methanol is added to a final concentration of 0.5% to maintain induction, and cells are harvested at a predetermined number of days post-induction. The resulting supernatant is decanted, and cell pellets frozen at −70° C. until protein extraction.

Total yeast intracellular protein is extracted as described above for the small-scale expression cell pellets except using 50 mL Breaking Buffer and 10 cycles of 30 seconds vortexing followed by 30 seconds on ice. The cell pellet lysates are then frozen at −70° C. overnight and are thawed followed by 10 cycles of 30 seconds vortexing and 30 seconds on ice. The protein solution is clarified by centrifugation, and the resulting solution is concentrated using Centricon Plus-70 Centrifugal Filter Devices (Millipore; 10,000 MWCO (Billerica, Mass.)) and freezing.

Recombinant RmAQP2 is purified using the 6×-Histidine tag and the ProBond Purification System (Thermo Fisher Scientific, Waltham, Mass.) using PROBOND nickel-chelating resin under native conditions according to manufacturer's recommended protocols. Eluted protein is concentrated using Amicon Ultra-15 (10,000 MWCO) centrifugation units. RmAQP2 is quantified by the Bio-Rad Protein Assay Kit I with bovine plasma gamma globulin protein standards (Hercules, Calif.), and purity is verified by gel electrophoresis as described above. Protein identity is verified by mass spectrometry analysis and Western blotting, taking advantage of the c-myc and 6× His tag epitopes on the recombinant RmAQP2 that exist because of the expression vector sequence. The WesternBreeze Chromogenic Kit and Anti-myc-HRP and Anti-His(C-term)-HRP antibodies (Thermo Fisher Scientific, Waltham, Mass.) are utilized using manufacturer's recommended protocols. Alkaline phosphatase-conjugated secondary antibody is utilized to enhance sensitivity.

EXAMPLE 7

Assessment of Efficacy of Immunogenic Composition Containing RmAQP2

Controlled pen trials are conducted to evaluate the immunogenic and protective capacity of RmAQP2. Recombinant RmAQP2 is adjuvated with Montanide ISA 61 VG (Seppic, Paris) which is a water in oil emulsion into doses of 2 ml containing approximately 200 µg recombinant RmAQP2. One-year-old Holstein calves are randomly distributed into groups of six animals each. Negative controls are injected with adjuvant alone. All animals are injected intramuscularly at 0, 2 and 4 weeks. Serum samples are taken from each animal before immunization and weekly thereafter. Twenty-one days after the last injection the animals are challenged with 15,000 *R. microplus* larvae. These larvae are delivered in three applications of 5,000 larvae each during one week, placed in separate vials onto the back of the animals. As engorged female ticks detached, they are collected once a day, weighed, and incubated at 29° C. and 85% humidity until egg laying is complete. Eggs are weighed and incubated at 29° C. and 85% humidity to allow hatching so as to determine the eclosion percentage.

Bovine blood is sampled weekly, and separated serum is frozen until analyzed by ELISA. For the ELISA, sera from each group are pooled according to day of collection. Microtiter plates are coated with RmAQP2 (50 μl per well of a 1 μg RmAQP2/ml solution in 20 mM sodium carbonate buffer, pH 9.6) and are incubated overnight at 4° C. Blocking with 2% bovine serum albumin in PBS-T is followed by washing five times with PBS pH 7.4. The plates are incubated for 45 minutes at 37° C. with 100 μl per well of immunized bovine serum diluted to 1:100 in PBS. After washing, 50 μl of rabbit anti-bovine IgG peroxidase conjugate (Sigma Aldrich, St. Louis, Mo.) diluted to 1:20,000 are added, and the plate is incubated for 30 minutes at room temperature. After incubation and washing, 50 μl of chromogenic substrate o-phenylenediamine (1.0 mM) are added, and the reaction is stopped after 15 minutes by adding 50 μl of NaOH (0.2 M). A microplate reader is used to assess the results with absorbance set at 490 nm.

EXAMPLE 8

Assessment of Efficacy of Immunogenic Composition Containing Fragments of RmAQP2

Next, an assessment of the efficacy of RmAQP2 peptides (Peptide 2 (SEQ ID NO: 14), Peptide 3 (SEQ ID NO: 15), and (Peptide 4 (SEQ ID NO: 27) to generate an immune response in an animal which reduces *R. microplus* reproduction fitness and/or *R. microplus* survival and/or reduce tick-borne diseases. Peptide 2, Peptide 3, and Peptide 4 are chemically synthesized and conjugated to keyhole limpet hemocyanin (KLH) by adding a cystine-KLH to the N-terminal end of the peptide; synthesis and conjugation of the peptides is performed by a commercial lab (NeoScientific, Woburn, Mass.). For the experiments described below, 50 µg of each of Peptide 2, Peptide 3, and Peptide 4 are individually emulsified in 1.0 ml of a 10 mg/ml solution of saponin adjuvant (Quil A™, InvivoGen, San Diego, Calif.). Equivalent volume of Quil A™ is used as negative control. Each experiment uses a blocked design; each block contains 3 male Holstein calves (3-4 months of age) each calf receiving three separate injections at three different injection sites: one injection of Peptide 2, one injection of Peptide 3, and one injection of Peptide 4, prepared as described above, and 3 male Holstein calves (3-4 months of age) receiving only adjuvant as a control (also at three different injection sites). The two groups of calves are immunized subcutaneously three to four times (depending on titers) at 21 day intervals. Serum antibody titers and isotypes against RmAQP2 are monitored by Western blot and/or ELISA prior to challenging the immunized calves with female *R. microplus*.

In one experiment, three weeks after the last immunization, larvae hatched from 0.25 grams of normal *R. microplus* (La Minita strain) eggs (≈5,000 larvae) are applied to each calf under cloth tick feeding patches. To assess feeding success engorged female ticks are collected daily, counted, and a representative sample are weighed to determine average daily replete weight. A sample of ticks is rinsed in tap water, and incubated individually at 26° C. and 96% relative humidity to allow for egg laying. The total number of ticks feeding to repletion, average replete weight, weight of eggs laid, and the hatching success of eggs laid by each female is assessed. A group of larvae are held to determine larval survival at monthly intervals after hatching.

In a second experiment, the effectiveness of the peptides are assessed after infecting the calves with *Babesia bovis*. After immunizing the calves with peptides as described above, *R. microplus* larvae are applied to the calves (as described above), and the calves are infected with frozen blood stabilates of *B. bovis*. Clinical signs of infection, including parasitemia and PCV, are monitored daily in all infected animals. Tick feeding success is assessed by counting the number of successfully engorged female ticks and determining the average daily replete weight (as described above). A sample of ticks is rinsed in tap water, and incubated individually at 26° C. and 96% relative humidity to allow for egg laying. After laying eggs these ticks are tested for the presence of *B. bovis* infection by hemolymph smear, and the average weight of eggs laid by each female and the hatching success are assessed. A group of larvae are held to determine larval survival at monthly intervals after hatching.

Next, serum from immunized cattle are tested via immuno-blots to determine if antibodies in the serum bind to one, two, or all three peptides. If one or two of the peptides are primarily responsible for the immune response, the specific one or two peptides identified are used to immunize calves per the above protocol to assess if that one or two peptides generate sufficient protection when used alone or in combination with each other.

Not wishing to be bound to any particular theory, it is believed that the antibodies generated by each RmAQP2 peptide in vaccinated cattle bind to the extracellular domains of the RmAQP2 in the salivary glands of the tick, interfering with aquaporin channel function and reducing feeding success. Thus, immunogenic compositions containing one or more of Peptide 1, Peptide 2, Peptide 3, and/or Peptide 4 can reduce *R. microplus* reproductive viability and disease transmission.

We, the inventors, claim as follows:

1. An immunogenic composition comprising a pharmaceutically acceptable carrier and a *Rhipicephalus microplus* immunogen, wherein said *R. microplus* immunogen is present in an amount effective to stimulate an immune response in an ungulate to said *R. microplus* immunogen, wherein said *R. microplus* immunogen is selected from the group consisting of (a) an aquaporin 2 comprising amino acids 3-293 of SEQ ID NO: 2 , (b) a protein comprising an amino acid sequence that is at least 95% identical to amino acids 3-293 of SEQ ID NO: 2, (c) an aquaporin 2 protein comprising SEQ ID NO: 7, (d) an aquaporin 2 protein comprising SEQ ID NO: 9, (e) an aquaporin 2 peptide of SEQ ID NO: 13, (f) an aquaporin 2 peptide of SEQ ID NO: 14, (g) an aquaporin 2 peptide of SEQ ID NO: 15, (h) an aquaporin 2 peptide of SEQ ID NO: 27, and (i) a combination thereof; and wherein said carrier is selected from the group consisting of phosphate buffered saline, lactose, dextrose, sucrose, sorbitol, mannitol, starch, acacia gum, calcium phosphate, calcium silicate, water, syrup, methyl hydroxybenzoate, propyl hydroxybenzoate, talc, stearic acid, magnesium, mineral oil, alginate, gelatin, microcrystalline cellulose, methyl cellulose, cellulose, polyvinylpyrrolidone, poly-lactic acid, poly-glycolic acid, poly-lactic-co-glycolic acid and a combination thereof.

2. The immunogenic composition of claim 1, further comprising an adjuvant.

3. The immunogenic composition of claim 2, wherein said adjuvant is selected from the group consisting of wherein said adjuvant is selected from the group consisting of saponin, mineral oil, vegetable oil, oil-in-water emulsion, water-in-oil emulsion, water-in-oil-in-water emulsion, aluminum hydroxide, aluminum phosphate, squalene, squalene-like compounds, Freund's complete adjuvant, Freund's incomplete adjuvant, muramyl dipeptide, monophosphoryl lipid A, polyphosphazine, *E. coli* LT, *E. coli* LT-B, *Vibrio cholera* toxin, CpG motif containing oligonucleotide, and a combination thereof.

4. A kit comprising a first container containing a *Rhipicephalus microplus* immunogen, instructions for administering said *R. microplus* immunogen to an ungulate, optionally a second container containing a pharmaceutically acceptable carrier, and optionally a third container containing an adjuvant; wherein said *R. microplus* immunogen is selected from the group consisting of (a) an aquaporin 2 comprising amino acids 3-293 of SEQ ID NO: 2, (b) a protein comprising an amino acid sequence that is at least 95% identical to amino acids 3-293 of SEQ ID NO: 2, (c) an aquaporin 2 protein comprising SEQ ID NO: 7, (d) an aquaporin 2 protein comprising SEQ ID NO: 9, (e) an aquaporin 2 peptide of SEQ ID NO: 13, (f) an aquaporin 2 peptide of SEQ ID NO: 14, (g) an aquaporin 2 peptide of SEQ ID NO: 15, (h) an aquaporin 2 peptide of SEQ ID NO: 27, and (i) a combination thereof.

5. A composition comprising a *R. microplus* immunogen comprising an amino acid sequence selected from the group consisting of SEQ ID NO: 2, SEQ ID NO: 5, SEQ ID NO: 7, SEQ ID NO: 9, SEQ ID NO: 13, SEQ ID NO: 14, SEQ ID NO: 15, and SEQ ID NO: 27, and an adjuvant, wherein said adjuvant is selected from the group consisting of saponin, mineral oil, vegetable oil, oil-in-water emulsion, water-in-oil emulsion, water-in-oil-in-water emulsion, aluminum hydroxide, aluminum phosphate, squalene, squalene-like compounds, Freund's complete adjuvant, Freund's incomplete adjuvant, muramyl dipeptide, monophosphoryl lipid A, polyphosphazine, *E. coli* LT, *E. coli* LT-B, *Vibrio cholera* toxin, CpG motif containing oligonucleotide, and a combination thereof.

6. An immunogenic composition comprising a pharmaceutically acceptable carrier and a *Rhipicephalus microplus* immunogen, wherein said *R. microplus* immunogen is present in an amount effective to stimulate an immune response in an ungulate to said *R. microplus* immunogen, wherein said *R. microplus* immunogen is selected from the group consisting of (a) an aquaporin 2 peptide of SEQ ID NO: 13, (b) an aquaporin 2 peptide of SEQ ID NO: 14, (c) an aquaporin 2 peptide of SEQ ID NO: 15, (d) an aquaporin 2 peptide of SEQ ID NO: 27, and (e) a combination thereof, wherein each of said aquaporin 2 peptide is conjugated to a carrier.

7. The composition of claim 6, wherein said carrier is selected from the group consisting of bovine serum albumin, keyhole limpet hemocyanin, ovalbumin, polylysine and a combination thereof.

8. The composition of claim 6, further comprising a pharmaceutically acceptable carrier.

9. The composition of claim 6, further comprising an adjuvant.

* * * * *

SEQUENCE LISTING

```
<160> NUMBER OF SEQ ID NOS: 28

<210> SEQ ID NO 1
<211> LENGTH: 1059
<212> TYPE: DNA
<213> ORGANISM: Rhipicephalus microplus

<400> SEQUENCE: 1
gatcagcagg acacggaatt cagcagcagg agaagccatg aagcccaaca ccgtgacccg      60
cgcttggcga caagtgaccg gatgctgcat cgagaacacg ctagctcgcc aggcgcttgc     120
cgagatggtg ggcactctcg tgctcaccct ggtcggcgac tgcgtgctcg cctctctcgc     180
cgtcttccag ctgggctccg tgggcctcgc tgccgcacct ctgggctggg gtctcgctgt     240
cttcctgggc gtgctggttg caggaggagt gtccggtgcc catctgaacc cggccgtcac     300
ggtcgccttg gccaccatcg gaaagcttgg ctggtgcaac gtgctcgcgt acgtcaccgc     360
acagtacctc ggtgctttcc tggcctccgg tctagtttac ctggtgtacg ccgacgcact     420
ttcccaggtg gacgtaaacc tcgctattgt gtacggcacc aacgccacgg ctccagtgtt     480
```

-continued

```
ctcctgcttt cctgctcccg gtgtgtcaac gctcacgtgc ctcctggatc aaactgtcag        540
cactgcagtg ctgctactcg gcatctgtgc aatcaccgat ggacgtaaca tggcggtatc        600
ccgcggccag cagcctctcc tcgtcggcct cacggtctcc gcctgcatgt acgccttctc        660
gtataactgc ggcaatccac tgaaccctgc tcgtgacctt gctccgagga tcttcacggc        720
catgtgtggc tggggctccg cagtgttttc cttccgctcg tacaattggt tttgggtgcc        780
ggtggtcggc ccgcaccttg gcgcagttat cggagtttgg atctacaaac tagccgtcga        840
caaccactgg aaggacgagg atgaagtaga tgaggatgag aaaagacccc tactctcaaa        900
tgcgaagatc tgcgcctgag gcctaccagc tcatgccacg gattgtatat gcgtagcctg        960
tgtatatcta tacacacata cgtaacttaa ccttttttgcg ttttagccgt atttccttct       1020
tatacatcta ataaatgctg agttttttat gcatcagta                              1059
```

<210> SEQ ID NO 2
<211> LENGTH: 293
<212> TYPE: PRT
<213> ORGANISM: Rhipicephalus microplus

<400> SEQUENCE: 2

```
Met Lys Pro Asn Thr Val Thr Arg Ala Trp Arg Gln Val Thr Gly Cys
1               5                   10                  15

Cys Ile Glu Asn Thr Leu Ala Arg Gln Ala Leu Ala Glu Met Val Gly
            20                  25                  30

Thr Leu Val Leu Thr Leu Val Gly Asp Cys Val Leu Ala Ser Leu Ala
        35                  40                  45

Val Phe Gln Leu Gly Ser Val Gly Leu Ala Ala Ala Pro Leu Gly Trp
    50                  55                  60

Gly Leu Ala Val Phe Leu Gly Val Leu Ala Gly Gly Val Ser Gly
65                  70                  75                  80

Ala His Leu Asn Pro Ala Val Thr Val Ala Leu Ala Thr Ile Gly Lys
                85                  90                  95

Leu Gly Trp Cys Asn Val Leu Ala Tyr Val Thr Ala Gln Tyr Leu Gly
            100                 105                 110

Ala Phe Leu Ala Ser Gly Leu Val Tyr Leu Val Tyr Ala Asp Ala Leu
        115                 120                 125

Ser Gln Val Asp Val Asn Leu Ala Ile Val Tyr Gly Thr Asn Ala Thr
    130                 135                 140

Ala Pro Val Phe Ser Cys Phe Pro Ala Pro Gly Val Ser Thr Leu Thr
145                 150                 155                 160

Cys Leu Leu Asp Gln Thr Val Ser Thr Ala Val Leu Leu Leu Gly Ile
                165                 170                 175

Cys Ala Ile Thr Asp Gly Arg Asn Met Ala Val Ser Arg Gly Gln Gln
            180                 185                 190

Pro Leu Leu Val Gly Leu Thr Val Ser Ala Cys Met Tyr Ala Phe Ser
        195                 200                 205

Tyr Asn Cys Gly Asn Pro Leu Asn Pro Ala Arg Asp Leu Ala Pro Arg
    210                 215                 220

Ile Phe Thr Ala Met Cys Gly Trp Gly Ser Ala Val Phe Ser Phe Arg
225                 230                 235                 240

Ser Tyr Asn Trp Phe Trp Val Pro Val Val Gly Pro His Leu Gly Ala
                245                 250                 255

Val Ile Gly Val Trp Ile Tyr Lys Leu Ala Val Asp Asn His Trp Lys
            260                 265                 270
```

Asp Glu Asp Glu Val Asp Glu Asp Glu Lys Arg Pro Leu Leu Ser Asn
            275                 280                 285

Ala Lys Ile Cys Ala
    290

<210> SEQ ID NO 3
<211> LENGTH: 882
<212> TYPE: DNA
<213> ORGANISM: Rhipicephalus microplus

<400> SEQUENCE: 3

| | | | | | |
|---|---|---|---|---|---|
| atgaagccca | acaccgtgac | ccgcgcttgg | cgacaagtga | ccggatgctg | catcgagaac | 60 |
| acgctagctc | gccaggcgct | tgccgagatg | gtgggcactc | tcgtgctcac | cctggtcggc | 120 |
| gactgcgtgc | tcgcctctct | cgccgtcttc | cagctgggct | ccgtgggcct | cgctgccgca | 180 |
| cctctgggct | ggggtctcgc | tgtcttcctg | ggcgtgctgg | ttgcaggagg | agtgtccggt | 240 |
| gcccatctga | acccgccgt | cacggtcgcc | ttggccacca | tcggaaagct | tggctggtgc | 300 |
| aacgtgctcg | cgtacgtcac | cgcacagtac | ctcggtgctt | tcctggcctc | cggtctagtt | 360 |
| tacctggtgt | acgccgacgc | actttcccag | gtggacgtaa | acctcgctat | tgtgtacggc | 420 |
| accaacgcca | cggctccagt | gttctcctgc | tttcctgctc | ccggtgtgtc | aacgctcacg | 480 |
| tgcctcctgg | atcaaactgt | cagcactgca | gtgctgctac | tcggcatctg | tgcaatcacc | 540 |
| gatggacgta | acatggcggt | atcccgcggc | cagcagcctc | cctcgtcgg | cctcacggtc | 600 |
| tccgcctgca | tgtacgcctt | ctcgtataac | tgcggcaatc | cactgaaccc | tgctcgtgac | 660 |
| cttgctccga | ggatcttcac | ggccatgtgt | ggctggggct | ccgcagtgtt | ttccttccgc | 720 |
| tcgtacaatt | ggttttgggt | gccggtggtc | ggcccgcacc | ttggcgcagt | tatcggagtt | 780 |
| tggatctaca | aactagccgt | cgacaaccac | tggaaggacg | aggatgaagt | agatgaggat | 840 |
| gagaaaagac | ccctactctc | aaatgcgaag | atctgcgcct | ga | | 882 |

<210> SEQ ID NO 4
<211> LENGTH: 882
<212> TYPE: DNA
<213> ORGANISM: Artificial Sequence
<220> FEATURE:
<223> OTHER INFORMATION: RmAQP2 codon optimized for Pichia expression

<400> SEQUENCE: 4

| | | | | | |
|---|---|---|---|---|---|
| atgaagccaa | acactgttac | tagagcttgg | agacaagtta | ctggttgttg | tattgaaaac | 60 |
| actttggcta | gacaagcttt | ggctgaaatg | gttggtactt | tggttttgac | tttggttggt | 120 |
| gattgtgttt | tggcttcttt | ggctgttttt | caattgggtt | ctgttggttt | ggctgctgct | 180 |
| ccattgggtt | ggggtttggc | tgttttttg | ggtgttttgg | ttgctggtgg | tgtttctggt | 240 |
| gctcatttga | acccagctgt | tactgttgct | ttggctacta | ttggtaagtt | gggttggtgt | 300 |
| aacgttttgg | cttacgttac | tgctcaatac | ttgggtgctt | ttttggcttc | tggtttggtt | 360 |
| tacttggttt | acgctgatgc | tttgtctcaa | gttgatgtta | acttggctat | tgtttacggt | 420 |
| actaacgcta | ctgctccagt | ttttttcttgt | tttccagctc | caggtgtttc | tactttgact | 480 |
| tgtttgttgg | atcaaactgt | ttctactgct | gttttgttgt | tgggtatttg | tgctattact | 540 |
| gatggtagaa | acatggctgt | ttctagaggt | caacaaccat | tgttggttgg | tttgactgtt | 600 |
| tctgcttgta | tgtacgcttt | tcttacaac | tgtggtaacc | cattgaaccc | agctagagat | 660 |
| ttggctccaa | gaattttac | tgctatgtgt | ggttggggt | ctgctgtttt | ttctttaga | 720 |
| tcttacaact | ggttttgggt | tccagttgtt | ggtccacatt | tgggtgctgt | tattggtgtt | 780 |

```
tggatttaca agttggctgt tgataaccat tggaaggatg aagatgaagt tgatgaagat      840 gaaagagac cattgttgtc taacgctaag atttgtgctt aa                          882
```

<210> SEQ ID NO 5
<211> LENGTH: 293
<212> TYPE: PRT
<213> ORGANISM: Artificial Sequence
<220> FEATURE:
<223> OTHER INFORMATION: RmAQP2 optimized for Pichia expression

<400> SEQUENCE: 5

```
Met Lys Pro Asn Thr Val Thr Arg Ala Trp Arg Gln Val Thr Gly Cys
1               5                   10                  15

Cys Ile Glu Asn Thr Leu Ala Arg Gln Ala Leu Ala Glu Met Val Gly
                20                  25                  30

Thr Leu Val Leu Thr Leu Val Gly Asp Cys Val Leu Ala Ser Leu Ala
            35                  40                  45

Val Phe Gln Leu Gly Ser Val Gly Leu Ala Ala Pro Leu Gly Trp
    50                  55                  60

Gly Leu Ala Val Phe Leu Gly Val Leu Val Ala Gly Gly Val Ser Gly
65                  70                  75                  80

Ala His Leu Asn Pro Ala Val Thr Val Ala Leu Ala Thr Ile Gly Lys
                85                  90                  95

Leu Gly Trp Cys Asn Val Leu Ala Tyr Val Thr Ala Gln Tyr Leu Gly
            100                 105                 110

Ala Phe Leu Ala Ser Gly Leu Val Tyr Leu Val Tyr Ala Asp Ala Leu
        115                 120                 125

Ser Gln Val Asp Val Asn Leu Ala Ile Val Tyr Gly Thr Asn Ala Thr
    130                 135                 140

Ala Pro Val Phe Ser Cys Phe Pro Ala Pro Gly Val Ser Thr Leu Thr
145                 150                 155                 160

Cys Leu Leu Asp Gln Thr Val Ser Thr Ala Val Leu Leu Leu Gly Ile
                165                 170                 175

Cys Ala Ile Thr Asp Gly Arg Asn Met Ala Val Ser Arg Gly Gln Gln
            180                 185                 190

Pro Leu Leu Val Gly Leu Thr Val Ser Ala Cys Met Tyr Ala Phe Ser
        195                 200                 205

Tyr Asn Cys Gly Asn Pro Leu Asn Pro Ala Arg Asp Leu Ala Pro Arg
    210                 215                 220

Ile Phe Thr Ala Met Cys Gly Trp Gly Ser Ala Val Phe Ser Phe Arg
225                 230                 235                 240

Ser Tyr Asn Trp Phe Trp Val Pro Val Gly Pro His Leu Gly Ala
                245                 250                 255

Val Ile Gly Val Trp Ile Tyr Lys Leu Ala Val Asp Asn His Trp Lys
            260                 265                 270

Asp Glu Asp Glu Val Asp Glu Asp Glu Lys Arg Pro Leu Leu Ser Asn
        275                 280                 285

Ala Lys Ile Cys Ala
    290
```

<210> SEQ ID NO 6
<211> LENGTH: 896
<212> TYPE: DNA
<213> ORGANISM: Artificial Sequence
<220> FEATURE:
<223> OTHER INFORMATION: EcoRI-RmAQP2-NotI codon optimized for Pichia expression

<400> SEQUENCE: 6

```
gaattcgaaa tggagccaaa cactgttact agagcttgga gacaagttac tggttgttgt      60
attgaaaaca ctttggctag acaagctttg gctgaaatgg ttggtacttt ggttttgact     120
ttggttggtg attgtgtttt ggcttctttg gctgtttttc aattgggttc tgttggtttg     180
gctgctgctc cattgggttg gggtttggct gttttttgg gtgttttggt tgctggtggt      240
gtttctggtg ctcatttgaa cccagctgtt actgttgctt tggctactat tggtaagttg     300
ggttggtgta acgttttggc ttacgttact gctcaatact tgggtgcttt tttggcttct     360
ggtttggttt acttggttta cgctgatgct ttgtctcaag ttgatgttaa cttggctatt     420
gtttacggta ctaacgctac tgctccagtt ttttcttgtt ttccagctcc aggtgtttct     480
actttgactt gtttgttgga tcaaactgtt tctactgctg ttttgttgtt gggtatttgt     540
gctattactg atggtagaaa catggctgtt tctagaggtc aacaaccatt gttggttggt     600
ttgactgttt ctgcttgtat gtacgctttt tcttacaact gtggtaaccc attgaaccca     660
gctagagatt tggctccaag aattttttact gctatgtgtg ttggggttc tgctgttttt    720
tcttttagat cttacaactg gttttgggtt ccagttgttg gtccacattt gggtgctgtt     780
attggtgttt ggatttacaa gttggctgtt gataaccatt ggaaggatga agatgaagtt     840
gatgaagatg aaaagagacc attgttgtct aacgctaaga tttgtgctgc ggccgc         896
```

<210> SEQ ID NO 7
<211> LENGTH: 295
<212> TYPE: PRT
<213> ORGANISM: Artificial Sequence
<220> FEATURE:
<223> OTHER INFORMATION: Open reading frame of EcoRI-RmAQP2-NotI codon optimized for Pichia expression

<400> SEQUENCE: 7

```
Met Glu Pro Asn Thr Val Thr Arg Ala Trp Arg Gln Val Thr Gly Cys
1               5                   10                  15

Cys Ile Glu Asn Thr Leu Ala Arg Gln Ala Leu Ala Glu Met Val Gly
            20                  25                  30

Thr Leu Val Leu Thr Leu Val Gly Asp Cys Val Leu Ala Ser Leu Ala
        35                  40                  45

Val Phe Gln Leu Gly Ser Val Gly Leu Ala Ala Pro Leu Gly Trp
    50                  55                  60

Gly Leu Ala Val Phe Leu Gly Val Leu Ala Gly Val Ser Gly
65                  70                  75                  80

Ala His Leu Asn Pro Ala Val Thr Val Ala Leu Ala Thr Ile Gly Lys
                85                  90                  95

Leu Gly Trp Cys Asn Val Leu Ala Tyr Val Thr Ala Gln Tyr Leu Gly
            100                 105                 110

Ala Phe Leu Ala Ser Gly Leu Val Tyr Leu Val Tyr Ala Asp Ala Leu
        115                 120                 125

Ser Gln Val Asp Val Asn Leu Ala Ile Val Tyr Gly Thr Asn Ala Thr
    130                 135                 140

Ala Pro Val Phe Ser Cys Phe Pro Ala Pro Gly Val Ser Thr Leu Thr
145                 150                 155                 160

Cys Leu Leu Asp Gln Thr Val Ser Thr Ala Val Leu Leu Leu Gly Ile
                165                 170                 175

Cys Ala Ile Thr Asp Gly Arg Asn Met Ala Val Ser Arg Gly Gln Gln
```

```
                180                 185                 190
Pro Leu Leu Val Gly Leu Thr Val Ser Ala Cys Met Tyr Ala Phe Ser
        195                 200                 205

Tyr Asn Cys Gly Asn Pro Leu Asn Pro Ala Arg Asp Leu Ala Pro Arg
        210                 215                 220

Ile Phe Thr Ala Met Cys Gly Trp Gly Ser Ala Val Phe Ser Phe Arg
225                 230                 235                 240

Ser Tyr Asn Trp Phe Trp Val Pro Val Gly Pro His Leu Gly Ala
                245                 250                 255

Val Ile Gly Val Trp Ile Tyr Lys Leu Ala Val Asp Asn His Trp Lys
            260                 265                 270

Asp Glu Asp Glu Val Asp Glu Asp Glu Lys Arg Pro Leu Leu Ser Asn
        275                 280                 285

Ala Lys Ile Cys Ala Ala Ala
        290                 295

<210> SEQ ID NO 8
<211> LENGTH: 963
<212> TYPE: DNA
<213> ORGANISM: Artificial Sequence
<220> FEATURE:
<223> OTHER INFORMATION: open reading frame of pPIC containing
      EcoRI-RmAQP2-NotI codon optimized for Pichia expression

<400> SEQUENCE: 8
atggagccaa acactgttac tagagcttgg agacaagtta ctggttgttg tattgaaaac        60
actttggcta acaagctttt ggctgaaatg gttggtactt tggttttgac tttggttggt       120
gattgtgttt tggcttcttt ggctgttttt caattgggtt ctgttggttt ggctgctgct       180
ccattgggtt gggttttggc tgttttttg ggtgttttgg ttgctggtgg tgtttctggt        240
gctcatttga acccagctgt tactgttgct ttggctacta ttggtaagtt gggttggtgt       300
aacgttttgg cttacgttac tgctcaatac ttgggtgctt ttttggcttc tggtttggtt      360
tacttggttt acgctgatgc tttgtctcaa gttgatgtta acttggctat gtttacggt       420 actaacgcta ctgctccagt tttttcttgt tttccagctc aggtgtttc tactttgact       480 tgtttgttgg atcaaactgt ttctactgct gttttgttgt gggtatttg tgctattact       540 gatggtagaa acatggctgt ttctagaggt caacaaccat gttggttgg tttgactgtt       600 tctgcttgta tgtacgcttt ttcttacaac tgtggtaacc cattgaaccc agctagagat       660
ttggctccaa gaattttac tgctatgtgt ggttggggt ctgctgtttt ttcttttaga        720
tcttacaact ggttttgggt tccagttgtt ggtccacatt tgggtgctgt tattggtgtt      780
tggatttaca gttggctgt tgataaccat tggaaggatg aagatgaagt tgatgaagat      840
gaaaagagac cattgttgtc taacgctaag atttgtgctg cggccgccag ctttctagaa       900
caaaaactca tctcagaaga ggatctgaat agcgccgtcg accatcatca tcatcatcat      960
tga                                                                     963

<210> SEQ ID NO 9
<211> LENGTH: 320
<212> TYPE: PRT
<213> ORGANISM: Artificial Sequence
<220> FEATURE:
<223> OTHER INFORMATION: translation of open reading of pPIC containing
      EcoRI-RmAQP2-NotI codon optimized for Pichia expression including
      HIS tag

<400> SEQUENCE: 9
```

```
Met Glu Pro Asn Thr Val Thr Arg Ala Trp Arg Gln Val Thr Gly Cys
1               5                   10                  15

Cys Ile Glu Asn Thr Leu Ala Arg Gln Ala Leu Ala Glu Met Val Gly
            20                  25                  30

Thr Leu Val Leu Thr Leu Val Gly Asp Cys Val Leu Ala Ser Leu Ala
            35                  40                  45

Val Phe Gln Leu Gly Ser Val Gly Leu Ala Ala Pro Leu Gly Trp
    50                  55                  60

Gly Leu Ala Val Phe Leu Gly Val Leu Val Ala Gly Val Ser Gly
65              70                  75                  80

Ala His Leu Asn Pro Ala Val Thr Val Ala Leu Ala Thr Ile Gly Lys
            85                  90                  95

Leu Gly Trp Cys Asn Val Leu Ala Tyr Val Thr Ala Gln Tyr Leu Gly
                100                 105                 110

Ala Phe Leu Ala Ser Gly Leu Val Tyr Leu Val Tyr Ala Asp Ala Leu
        115                 120                 125

Ser Gln Val Asp Val Asn Leu Ala Ile Val Tyr Gly Thr Asn Ala Thr
    130                 135                 140

Ala Pro Val Phe Ser Cys Phe Pro Ala Pro Gly Val Ser Thr Leu Thr
145                 150                 155                 160

Cys Leu Leu Asp Gln Thr Val Ser Thr Ala Val Leu Leu Gly Ile
                165                 170                 175

Cys Ala Ile Thr Asp Gly Arg Asn Met Ala Val Ser Arg Gly Gln Gln
            180                 185                 190

Pro Leu Leu Val Gly Leu Thr Val Ser Ala Cys Met Tyr Ala Phe Ser
        195                 200                 205

Tyr Asn Cys Gly Asn Pro Leu Asn Pro Ala Arg Asp Leu Ala Pro Arg
210                 215                 220

Ile Phe Thr Ala Met Cys Gly Trp Gly Ser Ala Val Phe Ser Phe Arg
225                 230                 235                 240

Ser Tyr Asn Trp Phe Trp Val Pro Val Val Gly Pro His Leu Gly Ala
                245                 250                 255

Val Ile Gly Val Trp Ile Tyr Lys Leu Ala Val Asp Asn His Trp Lys
        260                 265                 270

Asp Glu Asp Glu Val Asp Glu Asp Lys Arg Pro Leu Leu Ser Asn
    275                 280                 285

Ala Lys Ile Cys Ala Ala Ala Ser Phe Leu Glu Gln Lys Leu Ile
290                 295                 300

Ser Glu Glu Asp Leu Asn Ser Ala Val Asp His His His His His
305                 310                 315                 320
```

<210> SEQ ID NO 10
<211> LENGTH: 879
<212> TYPE: DNA
<213> ORGANISM: Artificial Sequence
<220> FEATURE:
<223> OTHER INFORMATION: degenerate RmAQP2 sequence

<400> SEQUENCE: 10

```
atgaagccma acacygtkac ymgmgcttgg mgacaagtka cyggwtgytg yatygaraac    60
ackytrgctm gmcargckyt kgcygaratg gtkggyacty tsgtkytsac yytggtyggy   120
gaytgygtky tsgcytctyt sgcygtytty carytgggyt cygtkggyyt sgctgcygcw   180
ccwytgggyt ggggtytsgc tgtyttyytg ggygtkytgg ttgcwggwgg wgtktcyggt   240
```

-continued

```
gcycatytga acccrgcygt yackgtygcy ttggcyacya tyggwaagyt kggytggtgy    300
aacgtkytsg cktacgtyac ygcwcartac ytsggtgctt tyytggcytc yggtytrgtt    360
tacytggtkt acgcygaygc wytktcycar gtkgaygtwa acytsgctat tgtktacggy    420
acyaacgcya ckgctccagt kttytcytgy tttccwgctc cmggtgtktc wackytsack    480
tgyytsytgg atcaaactgt ywsyactgcw gtkytgytry tsggyatytg tgcwatyacy    540
gatggwmgwa acatggckgt wtcymgmggy carcarccwy tsytsgtygg yytsackgty    600
tcygcytgya tgtacgcytt ytcktayaac tgyggyaayc caytgaaccc wgctmgwgay    660
ytkgctccra gratyttyac kgcyatgtgt ggytggggyt cygcwgtktt ttcyttymgm    720
tcktacaayt ggttttgggt kccrgtkgty ggyccrcayy tkggygcwgt tatyggwgtt    780
tggatytaca arytrgcygt ygayaaccay tggaaggayg argatgaagt wgatgargat    840
garaaragac cmytrytstc waaygckaag atytgygcy                         879

<210> SEQ ID NO 11
<211> LENGTH: 18
<212> TYPE: DNA
<213> ORGANISM: Rhipicephalus microplus

<400> SEQUENCE: 11
gtaagtcacc gcacagta                                                  18

<210> SEQ ID NO 12
<211> LENGTH: 17
<212> TYPE: DNA
<213> ORGANISM: Rhipicephalus microplus

<400> SEQUENCE: 12
tacacaatag cgaggtt                                                   17

<210> SEQ ID NO 13
<211> LENGTH: 10
<212> TYPE: PRT
<213> ORGANISM: Rhipicephalus microplus

<400> SEQUENCE: 13

Leu Gly Ser Val Gly Leu Ala Ala Ala Pro
1               5                   10

<210> SEQ ID NO 14
<211> LENGTH: 32
<212> TYPE: PRT
<213> ORGANISM: Rhipicephalus microplus

<400> SEQUENCE: 14

Ala Asp Ala Leu Ser Gln Val Asp Val Asn Leu Ala Ile Val Tyr Gly
1               5                   10                  15

Thr Asn Ala Thr Ala Pro Val Phe Ser Cys Phe Pro Ala Pro Gly Val
            20                  25                  30

<210> SEQ ID NO 15
<211> LENGTH: 19
<212> TYPE: PRT
<213> ORGANISM: Rhipicephalus microplus

<400> SEQUENCE: 15

Met Cys Gly Trp Gly Ser Ala Val Phe Ser Phe Arg Ser Tyr Asn Trp
1               5                   10                  15

Phe Trp Val
```

<210> SEQ ID NO 16
<211> LENGTH: 20
<212> TYPE: DNA
<213> ORGANISM: Rhipicephalus microplus

<400> SEQUENCE: 16
aattcagcag caggagaagc                                                 20

<210> SEQ ID NO 17
<211> LENGTH: 20
<212> TYPE: DNA
<213> ORGANISM: Rhipicephalus microplus

<400> SEQUENCE: 17
cggcgtacac caggtaaact                                                 20

<210> SEQ ID NO 18
<211> LENGTH: 397
<212> TYPE: DNA
<213> ORGANISM: Rhipicephalus microplus

<400> SEQUENCE: 18
aattcagcag caggagaagc catgaagccc aacaccgtga cccgcgcttg gcgacaagtg     60
accggatgct gcatcgagaa cacgctagct cgccaggcgc ttgccgagat ggtgggcact    120
ctcgtgctca ccctggtcgg cgactgcgtg ctcgcctctc tcgccgtctt ccagctgggc    180
tccgtgggcc tcgctgccgc acctctgggc tggggtctcg ctgtcttcct gggcgtgctg    240
gttgcaggag gagtgtccgg tgcccatctg aacccggccg tcacggtcgc cttggccacc    300
atcggaaagc ttggctggtg caacgtgctc gcgtacgtca ccgcacagta cctcggtgct    360
ttcctggcct ccggtctagt ttacctggtg tacgccg                             397

<210> SEQ ID NO 19
<211> LENGTH: 397
<212> TYPE: RNA
<213> ORGANISM: Rhipicephalus microplus

<400> SEQUENCE: 19
aauucagcag caggagaagc caugaagccc aacaccguga cccgcgcuug gcgacaagug     60
accggaugcu gcaucgagaa cacgcuagcu cgccaggcgc uugccgagau ggugggcacu    120
cucgugcuca cccuggucgg cgacugcgug cucgccucuc ucgccgucuu ccagcugggc    180
uccgugggcc ucgcugccgc accucugggc uggggucucg cugucuuccu gggcgugcug    240
guugcaggag gagugguccgg ugcccaucug aacccggccg ucacggucgc cuuggccacc    300
aucggaaagc uuggcugguq caacgugcuc gcguacguca ccgcacagua ccucggugcu    360
uuccuggccu ccggucuagu uuaccugguq uacgccg                             397

<210> SEQ ID NO 20
<211> LENGTH: 19
<212> TYPE: DNA
<213> ORGANISM: Rhipicephalus microplus

<400> SEQUENCE: 20
cctctcctcg tcggcctca                                                  19

<210> SEQ ID NO 21
<211> LENGTH: 20
<212> TYPE: DNA

<213> ORGANISM: Rhipicephalus microplus

<400> SEQUENCE: 21
cggctaaaac gcaaaaggt                                                    20

<210> SEQ ID NO 22
<211> LENGTH: 396
<212> TYPE: DNA
<213> ORGANISM: Rhipicephalus microplus

<400> SEQUENCE: 22
cctctcctcg tcggcctcac ggtctccgcc tgcatgtacg ccttctcgta taactgcggc      60
aatccactga accctgctcg tgaccttgct ccgaggatct tcacggccat gtgtggctgg     120
ggctccgcag tgttttcctt ccgctcgtac aattggtttt gggtgccggt ggtcggcccg     180
caccttggcg cagttatcgg agtttggatc tacaaactag ccgtcgacaa ccactggaag     240
gacgaggatg aagtagatga ggatgagaaa agacccctac tctcaaatgc gaagatctgc     300
gcctgaggcc taccagctca tgccacggat tgtatatgcg tagcctgtgt atatctatac     360
acacatacgt aacttaacct ttttgcgttt tagccg                               396

<210> SEQ ID NO 23
<211> LENGTH: 396
<212> TYPE: RNA
<213> ORGANISM: Rhipicephalus microplus

<400> SEQUENCE: 23
ccucuccucg ucggccucac ggucuccgcc ugcauguacg ccuucucgua uaacugcggc      60
aauccacuga acccugcucg ugaccuugcu ccgaggaucu ucacggccau guguggcugg     120
ggcuccgcag uguuuuccuu ccgcucguac aauugguuuu ggguguggu ggucggcccg      180 caccuuggcg caguuaucgg aguuuggauc uacaaacuag ccgucgacaa ccacuggaag     240
gacgaggaug aaguagauga ggaugagaaa agaccccuac ucucaaaugc gaagaucugc     300
gccugaggcc uaccagcuca ugccacggau uguauaugcg uagccugugu auaucuauac     360
acacauacgu aacuuaaccu uuuugcguuu uagccg                               396

<210> SEQ ID NO 24
<211> LENGTH: 30
<212> TYPE: DNA
<213> ORGANISM: Rhipicephalus microplus

<400> SEQUENCE: 24
ctgggctccg tgggcctcgc tgccgcacct                                       30

<210> SEQ ID NO 25
<211> LENGTH: 99
<212> TYPE: DNA
<213> ORGANISM: Rhipicephalus microplus

<400> SEQUENCE: 25
gccgacgcac tttcccaggt ggacgtaaac ctcgctattg tgtacggcac caacgccacg      60
gctccagtgt tctcctgctt tcctgctccc ggtgtgtgt                             99

<210> SEQ ID NO 26
<211> LENGTH: 57
<212> TYPE: DNA
<213> ORGANISM: Rhipicephalus microplus

<400> SEQUENCE: 26

```
atgtgtggct ggggctccgc agtgttttcc ttccgctcgt acaattggtt ttgggtg        57

<210> SEQ ID NO 27
<211> LENGTH: 14
<212> TYPE: PRT
<213> ORGANISM: Rhipicephalus microplus

<400> SEQUENCE: 27

Ala Val Phe Gln Leu Gly Ser Val Gly Leu Ala Ala Ala Pro
1               5                   10

<210> SEQ ID NO 28
<211> LENGTH: 42
<212> TYPE: DNA
<213> ORGANISM: Rhipicephalus microplus

<400> SEQUENCE: 28
gccgtcttcc agctgggctc cgtgggcctc gctgccgcac ct                       42
```